(12) United States Patent
Parihar

(10) Patent No.: US 8,083,687 B2
(45) Date of Patent: Dec. 27, 2011

(54) TISSUE BIOPSY DEVICE WITH ROTATABLY LINKED THUMBWHEEL AND TISSUE SAMPLE HOLDER

(75) Inventor: Shailendra K. Parihar, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 506 days.

(21) Appl. No.: 12/337,997

(22) Filed: Dec. 18, 2008

(65) Prior Publication Data

US 2010/0160826 A1    Jun. 24, 2010

(51) Int. Cl.
*A61B 10/00*    (2006.01)
(52) U.S. Cl. .......................................... 600/568
(58) Field of Classification Search ............... 600/562, 600/564–568
See application file for complete search history.

(56) References Cited

U.S. PATENT DOCUMENTS

| | | | |
|---|---|---|---|
| 4,294,254 A | 10/1981 | Chamness | |
| 5,526,822 A | 6/1996 | Burbank et al. | |
| 5,873,886 A | 2/1999 | Larsen et al. | |
| 6,086,544 A | 7/2000 | Hibner et al. | |
| 6,626,849 B2 | 9/2003 | Huitema et al. | |
| 6,993,375 B2 | 1/2006 | Burbank et al. | |
| 6,996,433 B2 | 2/2006 | Burbank et al. | |
| 7,047,063 B2 | 5/2006 | Burbank et al. | |
| 7,442,171 B2 | 10/2008 | Stephens et al. | |
| 7,465,279 B2 | 12/2008 | Beckman et al. | |
| 2004/0054299 A1 | 3/2004 | Burdorff et al. | |
| 2007/0032742 A1 | 2/2007 | Monson et al. | |
| 2008/0195066 A1 | 8/2008 | Speeg et al. | |
| 2008/0214955 A1 | 9/2008 | Speeg et al. | |
| 2008/0221480 A1* | 9/2008 | Hibner et al. | 600/566 |

FOREIGN PATENT DOCUMENTS

| | | |
|---|---|---|
| EP | 0 736 285 | 10/1996 |
| EP | 1 932 481 | 6/2008 |

OTHER PUBLICATIONS

U.S. Appl. No. 12/038,359, filed Feb. 27, 2008, Speeg et al.
U.S. Appl. No. 12/337,674, filed Dec. 18, 2008, Parihar et al.
U.S. Appl. No. 12/337,814, filed Dec. 18, 2008, Parihar et al.
U.S. Appl. No. 12/337,872, filed Dec. 18, 2008, Parihar et al.
U.S. Appl. No. 12/337,874, filed Dec. 18, 2008, Parihar et al.
U.S. Appl. No. 12/337,911, filed Dec. 18, 2008, Parihar et al.
U.S. Appl. No. 12/337,942, filed Dec. 18, 2008, Parihar et al.
U.S. Appl. No. 60/869,736, filed Dec. 13, 2006, Ritchie et al.
U.S. Appl. No. 60/874,792, filed Dec. 13, 2006, Hibner et al.

(Continued)

*Primary Examiner* — Brian Szmal
(74) *Attorney, Agent, or Firm* — Frost Brown Todd LLC

(57) ABSTRACT

A biopsy device comprises a probe operably coupled with a holster. The probe comprises a needle portion, a body portion, a rotatable thumbwheel, a cutter, and a rotatable tissue sample holder. The needle portion has a tissue receiving aperture. The needle portion extends distally from the body portion. The thumbwheel is fixedly secured relative to the needle portion such that the thumbwheel is operable to rotate the needle portion about its longitudinal axis. The cutter is longitudinally movable within the needle portion and is configured to cut tissue protruding into the aperture. The rotatable tissue sample holder is configured to receive tissue samples severed by the cutter and communicated through the cutter lumen. The holster comprises a linking mechanism. The thumbwheel is coupled with the tissue sample holder via the linking mechanism such that the thumbwheel is manually rotatable to rotate the tissue sample holder via the linking mechanism.

17 Claims, 22 Drawing Sheets

OTHER PUBLICATIONS

International Search Report dated Feb. 17, 2010 for Application No. PCT/US2009/067306.
International Search Report dated Feb. 17, 2010 for Application No. PCT/US2009/067140.
International Preliminary Report on Patentability dated Jun. 21, 2011 for Application No. PCT/US2009/067306.
International Preliminary Report on Patentability dated Jun. 21, 2011 for Application No. PCT/US2009/067140.

* cited by examiner

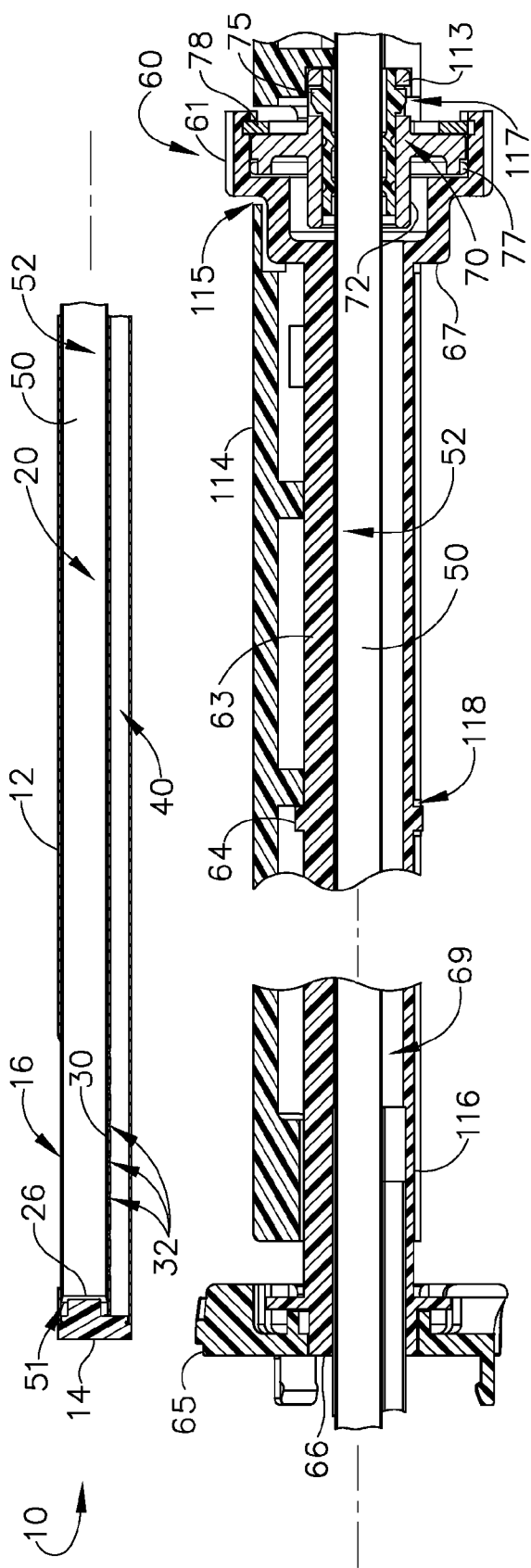
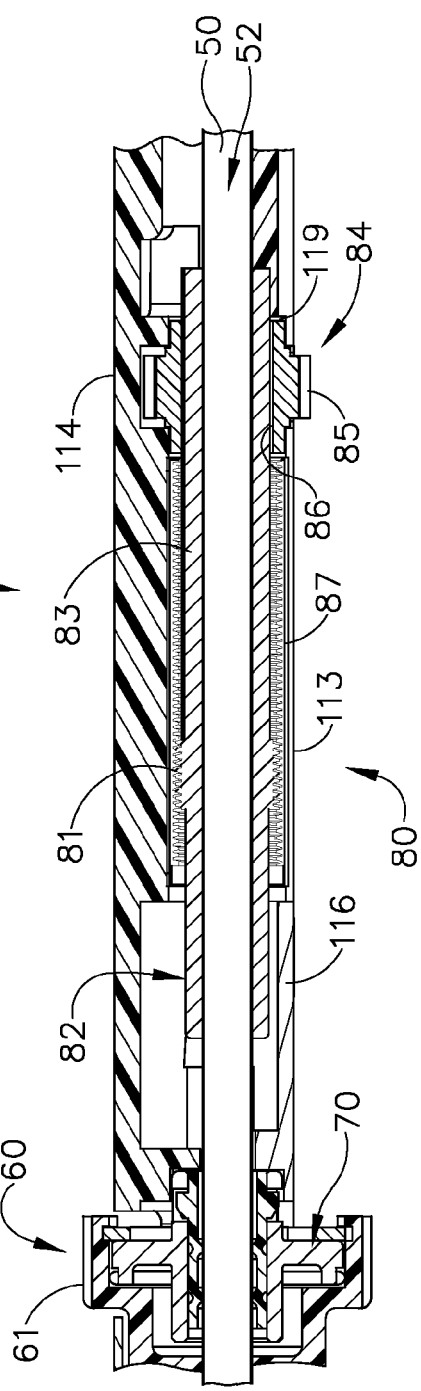
FIG. 6
FIG. 7

TISSUE BIOPSY DEVICE WITH ROTATABLY LINKED THUMBWHEEL AND TISSUE SAMPLE HOLDER

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Provisional Patent Application Ser. No. 60/869,736, entitled "Biopsy System," filed Dec. 13, 2006; and U.S. Provisional Patent Application Ser. No. 60/874,792, entitled "Biopsy Sample Storage," filed Dec. 13, 2006. The disclosure of each of the above-cited U.S. Patents, U.S. Patent Application Publications, and U.S. Provisional Patent Applications is incorporated by reference herein. While several systems and methods have been made and used for obtaining a biopsy sample, it is believed that no one prior to the inventors has made or used the invention described in the appended claims.

BRIEF DESCRIPTION OF THE FIGURES

While the specification concludes with claims which particularly point out and distinctly claim the invention, it is believed the present biopsy device will be better understood from the following description of certain examples taken in conjunction with the accompanying drawings, in which like reference numerals identify the same elements and in which:

FIG. 6 is an enlarged side cross-sectional view of a portion of the probe of FIG. 2, showing a rotational assembly extending from the central rotation knob to the needle;

FIG. 7 is an enlarged side cross-sectional view of a portion of the probe of FIG. 2, showing a cutter drive assembly;

DETAILED DESCRIPTION

Figure 1:
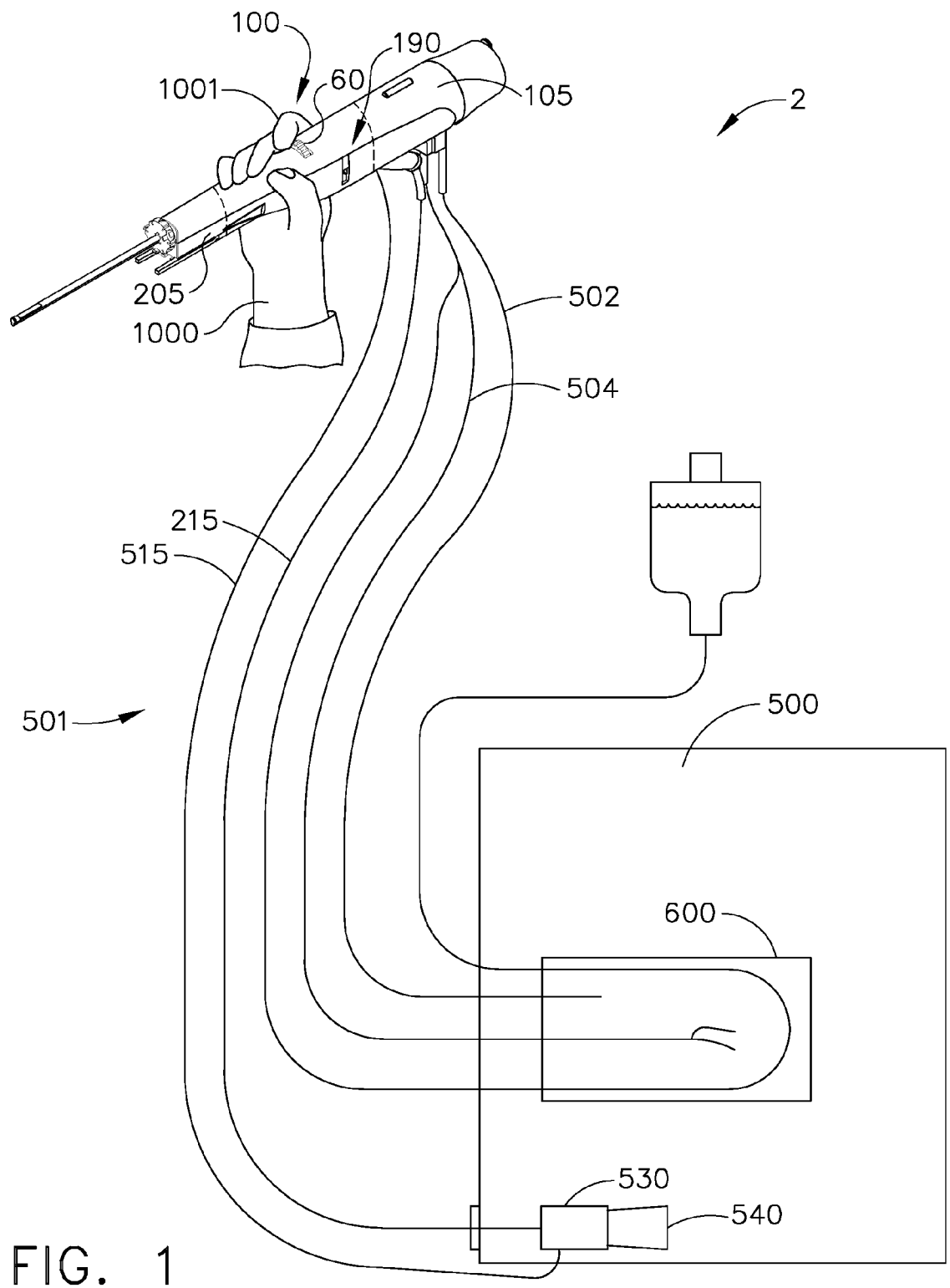
FIG. 1 is a schematic view of an exemplary biopsy system being operated with a single hand and with a finger rotating a central rotation knob to rotate a needle extending from a probe.

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Several merely illustrative examples of biopsy devices (100) (e.g., a probe (105) in combination with various holsters (205, 305, 705, 805, 905), etc.) will be described in greater detail below. It should be understood, however, that components, features, functionalities, methods of operation, contexts of use, etc. may be switched among the various examples of biopsy devices (100) as desired. For instance, features or components of one particular holster (205, 305, 705, 805, 905) example may be described in detail herein, while not necessarily being explicitly described herein in the context of another holster (205, 305, 705, 805, 905) example. This should not be read as implying that such features or components are excluded from all versions of the other holster (205, 305, 705, 805, 905) examples or of other combinations of probe (105) with any other holsters (205, 305, 705, 805, 905). Instead, repetition of certain components, features, functionalities, methods of operation, contexts of use, etc., will be avoided for the sake of brevity, it being understood that such components, features, functionalities, methods of operation, contexts of use, etc. may be applied to all biopsy devices (100) (e.g., all combinations of probe (105) with various holsters (205, 305, 705, 805, 905), etc.) unless such crossover is clearly inconsistent with certain versions of biopsy device (100).

I. A First Exemplary Biopsy Device

Figure 2:
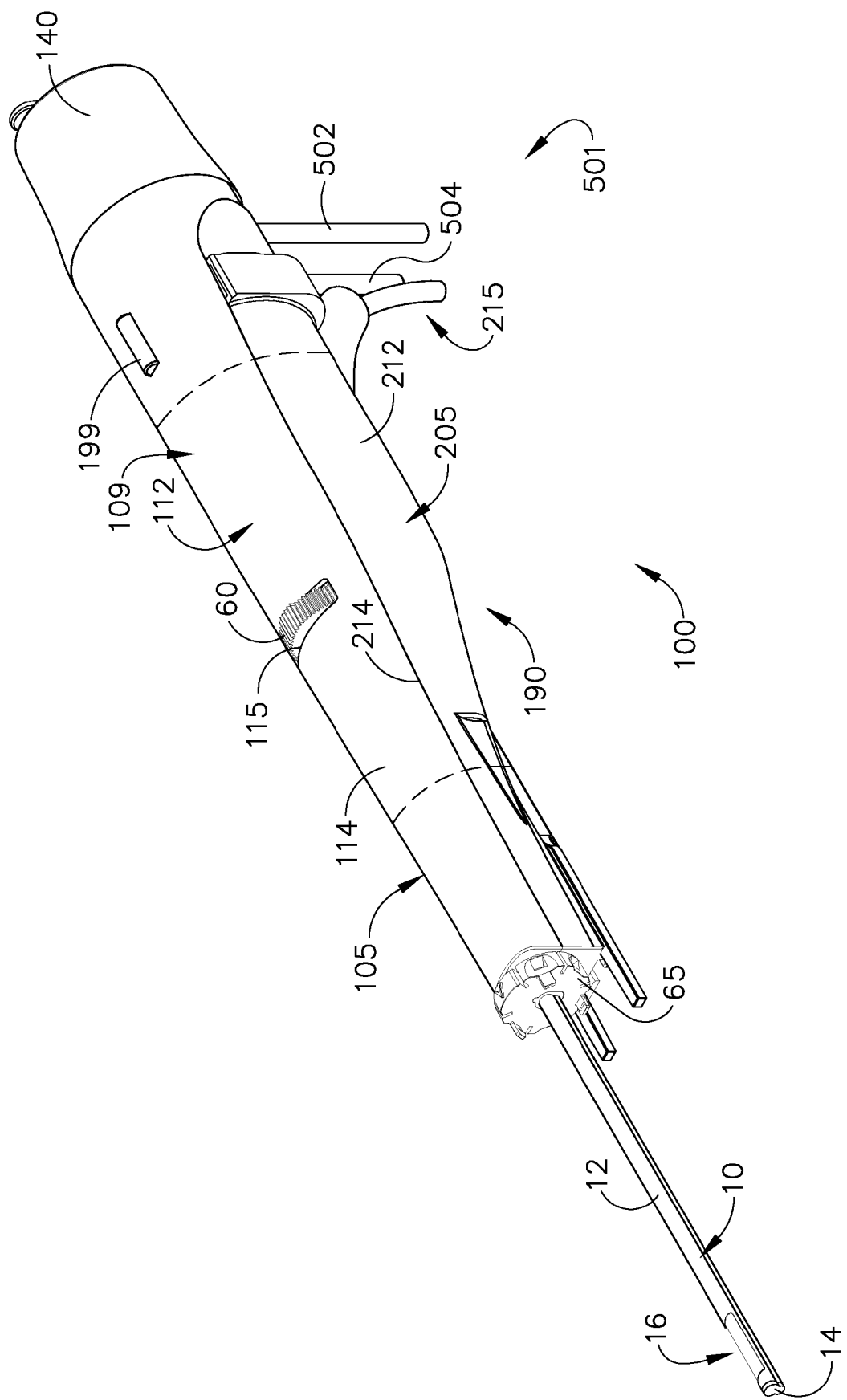
FIG. 2 is an isometric view of a biopsy device of the biopsy system of FIG. 1.
Figure 3:
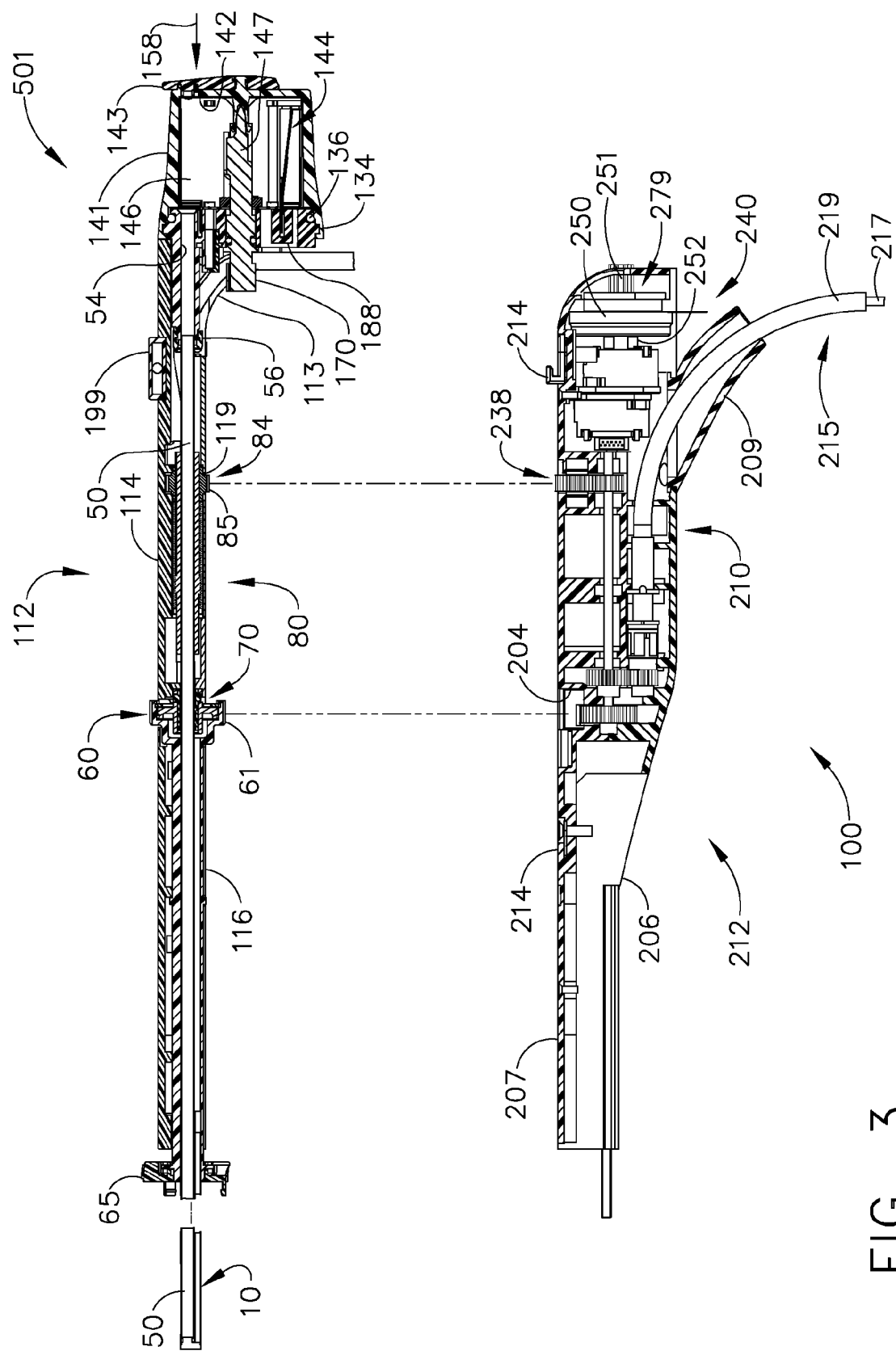
FIG. 3 is a side cross-sectional view of the biopsy device of FIG. 2, with a probe portion separated from a holster portion.
Figure 4:
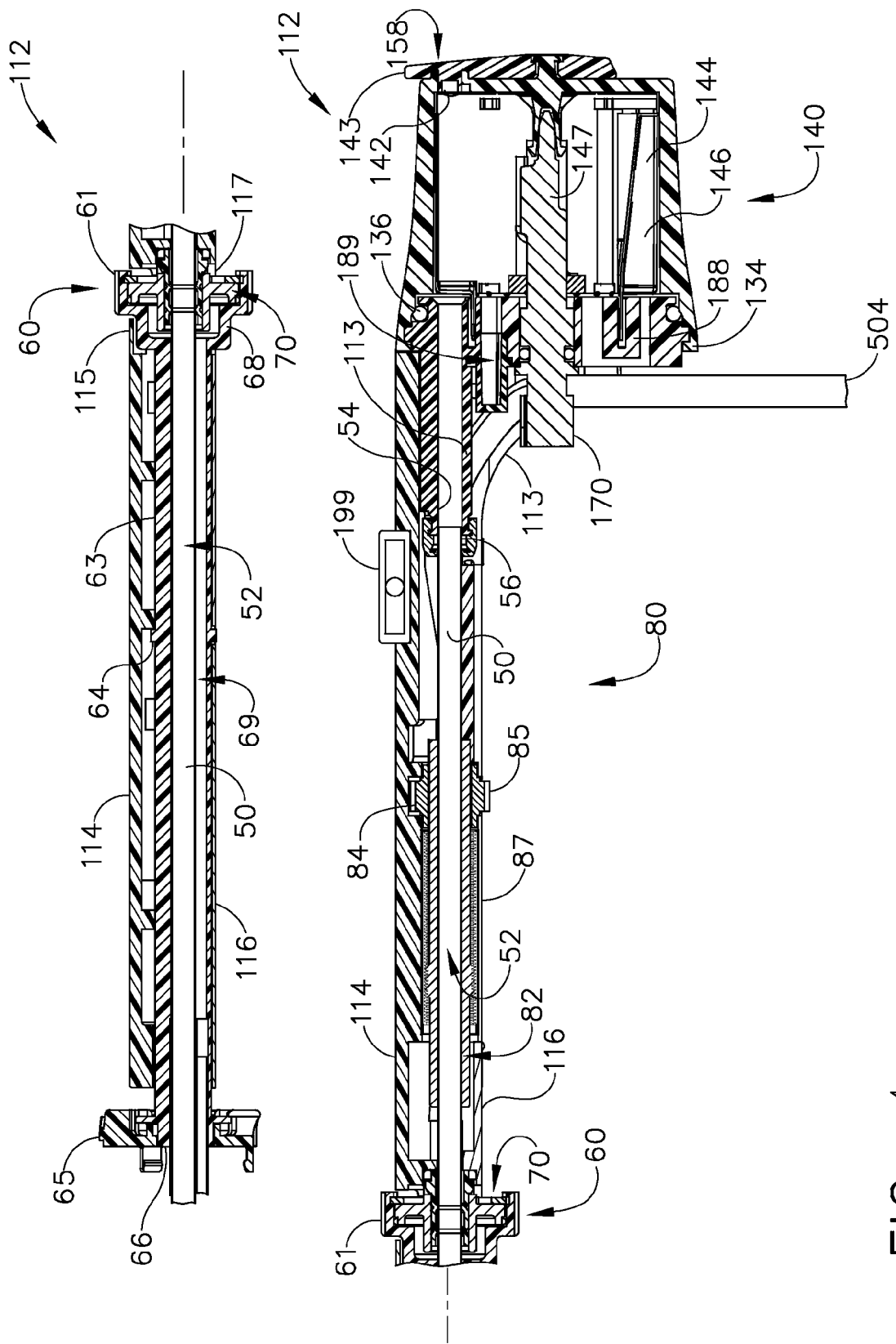
FIG. 4 is an enlarged side cross-sectional view of the probe of FIG. 2.

As shown in FIG. 1, an exemplary biopsy system (2) includes a biopsy device (100) for cutting and storing tissue samples acquired from a patient and a vacuum control module (500). As shown in FIGS. 2-4, biopsy device (100) of the present example comprises probe (105) and holster (205). Conduits (501) operatively attach to biopsy device (100) and extend between biopsy device (100) and vacuum control module (500). Biopsy device (100) of the present example is sized and balanced for single handed operation, and comprises a needle portion (10) extending distally therefrom for inserting into a patient and acquiring tissue samples from the patient. Needle portion (10) is longitudinally constrained yet rotatable relative the remainder of biopsy device (100), though in other versions needle portion (10) may be non-rotatable and/or operable to translate longitudinally relative the remainder of biopsy device (100). As will become apparent in view of the teachings herein, some versions of biopsy device (100) may offer size reductions, improved balance, and enhanced single handed grasping of biopsy device (100) with an operator or surgeon's hand (1000). For instance, biopsy device (100) may be operated in a handheld fashion under ultrasonic imaging guidance.

As will be described in greater detail below, needle portion (10) is operably connected to an exemplary central thumbwheel (60) that may be accessed and rotated by a finger (1001) or thumb of the operator's grasping hand (1000). When the operator or surgeon holds biopsy device (100) within one hand, rotation of central thumbwheel (60) (e.g., with a single finger or thumb) rotates needle portion (10) relative to the remainder of biopsy device (100) and within a desired portion of tissue. The single handed operation of the present example does not necessarily require rotation and/or repositioning of any of the operator's hands during use. Versions of biopsy device (100) may be compatible for use with magnetic resonance, x-ray, ultrasonic, PET/PEM, and/or other types of imaging systems. Indeed, while several examples herein relate to handheld use of biopsy device (100), it should be understood that biopsy device may be used in a variety of other ways. For instance, it will be appreciated in view of the disclosure herein that holster (205) may be configured to be mounted to a table, fixture, or other device, such as for use in a stereotactic or X-ray setting, an MRI setting, or any other setting. By way of example only, holster (205) may be coupled with a targeting set, such as the targeting set disclosed in U.S. Non-Provisional patent application Ser. No. [FBT DOCKET NO. 0021680.END6474USNP], entitled "MULTI-ORIENTATION TARGETING SET FOR MRI BIOPSY DEVICE," filed on even date herewith, the disclosure of which is incorporated by reference herein. Of course, it will be appreciated in view of the disclosure herein that biopsy device (100) may be used in a variety of other settings and combinations.

As will be described in greater detail below, probe (105) is separable from its corresponding holster (205). Use of the term "holster" herein should not be read as requiring any portion of probe (105) to be inserted into any portion of holster (205). Indeed, in some variations of biopsy device (100), probe (105) may simply sit on holster (205), with tissue sample holder (140) attached thereto. In some other variations, a portion of holster (205) may be inserted into probe (100) with tissue sample holder (140) attached thereto. Furthermore, in some biopsy devices (100), probe (105) and/or holster (205) and/or tissue sample holder (140) may be of unitary or integral construction, such that the components cannot be separated. Still other suitable structural and functional relationships between probe (105), holster (205), and tissue sample holder (140) will be apparent to those of ordinary skill in the art in view of the teachings herein.

Some variations of biopsy devices (100) may include one or more sensors (not shown), in probe (105) and/or in holster (205) that is/are configured to detect when probe (105) is coupled with holster (205). Such sensors or other features may further be configured to permit only certain types of probes (105) and holsters (205) to be coupled together. In addition or in the alternative, such sensors may be configured to disable one or more functions of probe (105) and/or holster (205) until a suitable probe (105) and holster (205) are coupled together. Of course, such sensors and features may be varied or omitted as desired.

By way of example only, probe (105) may be provided as a disposable component, while holster (205) may be provided as a reusable component. Vacuum control module (500) is provided on a cart (not shown) in the present example, though like other components described herein, a cart is merely optional. Among other components described herein, a footswitch (not shown) and/or other devices may be used to provide at least some degree of control of at least a portion of biopsy system (2). Conduits (501) provide communication of power (e.g., electrical, pneumatic, mechanical, etc.), control signals, saline, vacuum, and/or venting from vacuum control module (500) to biopsy device (100). One example of a vacuum control module (500) and how it may be used is disclosed in U.S. Pub. No. 2008/0195066, entitled "Revolving Tissue Sample Holder For Biopsy Device," published Aug. 14, 2008, the disclosure of which is incorporated by reference herein. In addition, an interface may be provided between vacuum control module (500) and biopsy device (100). Such an interface may be provided in accordance with the teachings of U.S. Non-Provisional patent application Ser. No. [FBT DOCKET NO. 0021680.END6466USNP], entitled "CONTROL MODULE INTERFACE," filed on even date herewith, the disclosure of which is incorporated by reference herein.

It should also be understood that any of the teachings herein may be readily incorporated with any of the teachings of U.S. Non-Provisional patent application Ser. No. [FBT DOCKET NO. 0021680.END6468USNP], entitled "BIOPSY DEVICE WITH SLIDING CUTTER COVER," filed on even date herewith, the disclosure of which is incorporated by reference herein. For instance, probe (105) may include any suitable features of any probes disclosed in U.S. Non-Provisional patent application Ser. No. [FBT DOCKET NO. 0021680.END6468USNP]. Suitable ways in which teachings herein and teachings in U.S. Non-Provisional patent application Ser. No. [FBT DOCKET NO. 0021680.END6468USNP] may be interchanged and incorporated with each other will be apparent to those of ordinary skill in the art in view of the teachings herein and in view of the teachings in U.S. Non-Provisional patent application Ser. No. [FBT DOCKET NO. 0021680.END6468USNP].

A. Exemplary Probe

As noted above, the assembly of probe (105) and holster (205) may be sized and configured for one handed operation, and may further be configured for one fingered rotation of central thumbwheel (60). In FIG. 2, probe (105) and holster (205) are shown releasably assembled together and ready for the acquisition of tissue samples from a patient. A grip area (190) is provided on probe (105) and holster (205) and is configured to fit within and to be grasped by a single hand (1000) of the operator or surgeon. Grip area (190) is indicated between dashed lines on FIG. 2, and may be sized, shaped, configured, textured, coated with non-skid coatings, roughened, and/or altered in a myriad of ways to enhance gripping between the operator's single hand (1000) and biopsy device (100). Of course, as noted above, biopsy device (100) need not necessarily be held in the hand (1000) of an operator during operation of biopsy device (100).

As shown in FIGS. 2-10, probe (105) of biopsy device (100) releasably attaches to holster (205). In FIG. 3, cross sections of unassembled probe (105) and holster (205) are shown spaced apart with extension lines extending between drive systems that engage together, and the reception of central thumbwheel (60) in a recess (204) in holster (205). The operative engagement of these components will be described in greater detail below.

Probe (105) of the present example comprises needle portion (10) at a distal end, a body portion (112) at a proximal end, and central thumbwheel (60). Needle portion (10) and body portion (112) define a longitudinal axis. Body portion (112) comprises a top cover (114), a bottom cover (116), and a proximal base (113). Central thumbwheel (60) extends through an opening (115) in top cover (114) and through an opening (117) in bottom cover (116). A needle orientation indicator (65) and central thumbwheel (60) are operably attached to needle portion (10) such that manual rotation of a central thumbwheel (60) by an operator rotates both needle orientation indicator (65) and needle portion (10). The location of central thumbwheel (60) in this example is at a longitudinal position just distal to a point of balance of biopsy device (100) so that the operator can grasp biopsy device (100) at the point of balance, and then extend one finger distally to rotate central thumbwheel (60), and hence, needle portion (10). Of course, central thumbwheel (60) may be located at any other suitable position on biopsy device (100). Furthermore, central thumbwheel (60) may be operated by an operator's thumb instead of, e.g., the operator's index finger.

Figure 8:
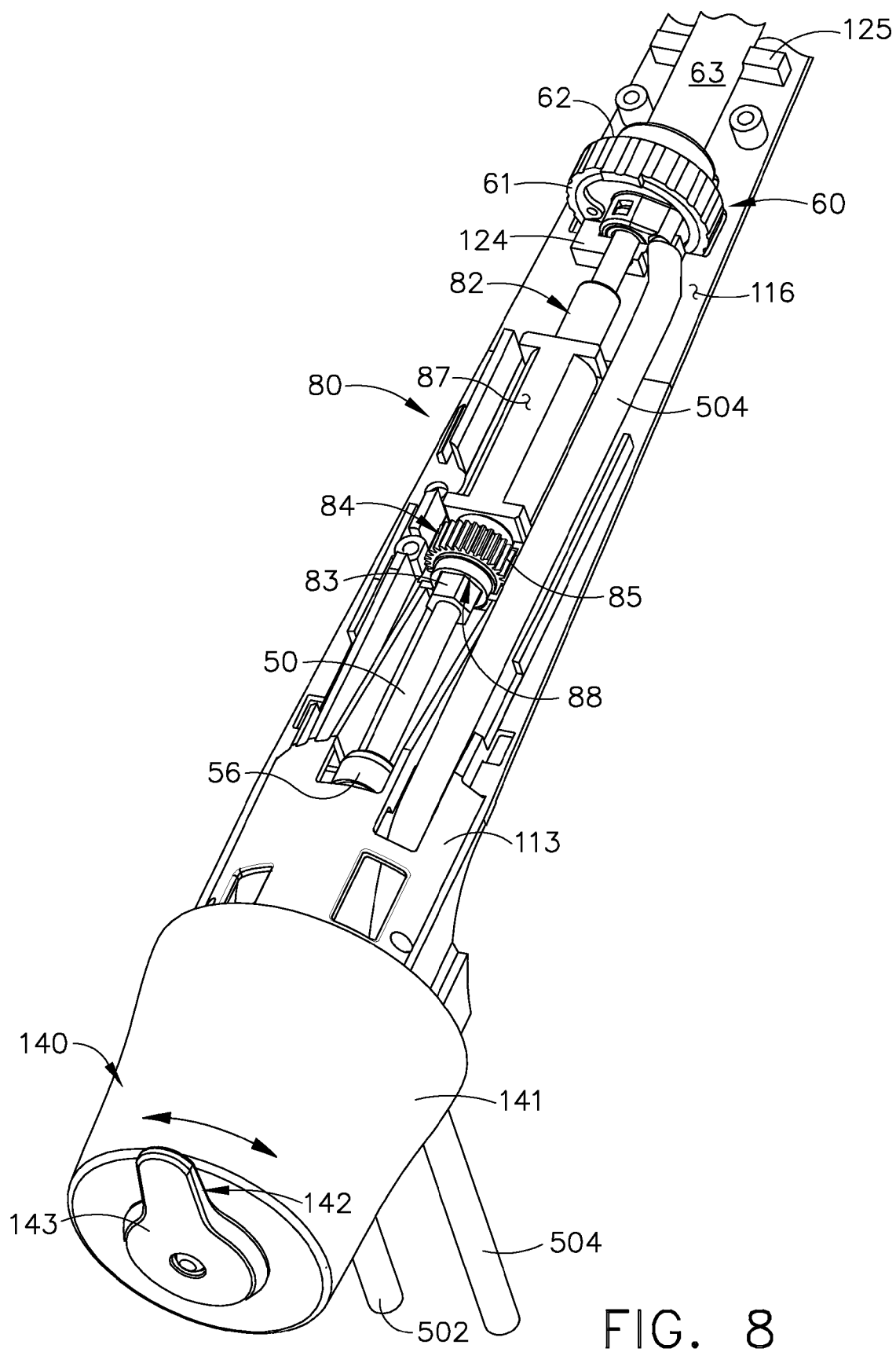
FIG. 8 is a partial perspective view of a proximal portion of the probe of FIG. 2, with the upper cover removed to show a vacuum manifold system and a cutter drive system.
Figure 9:
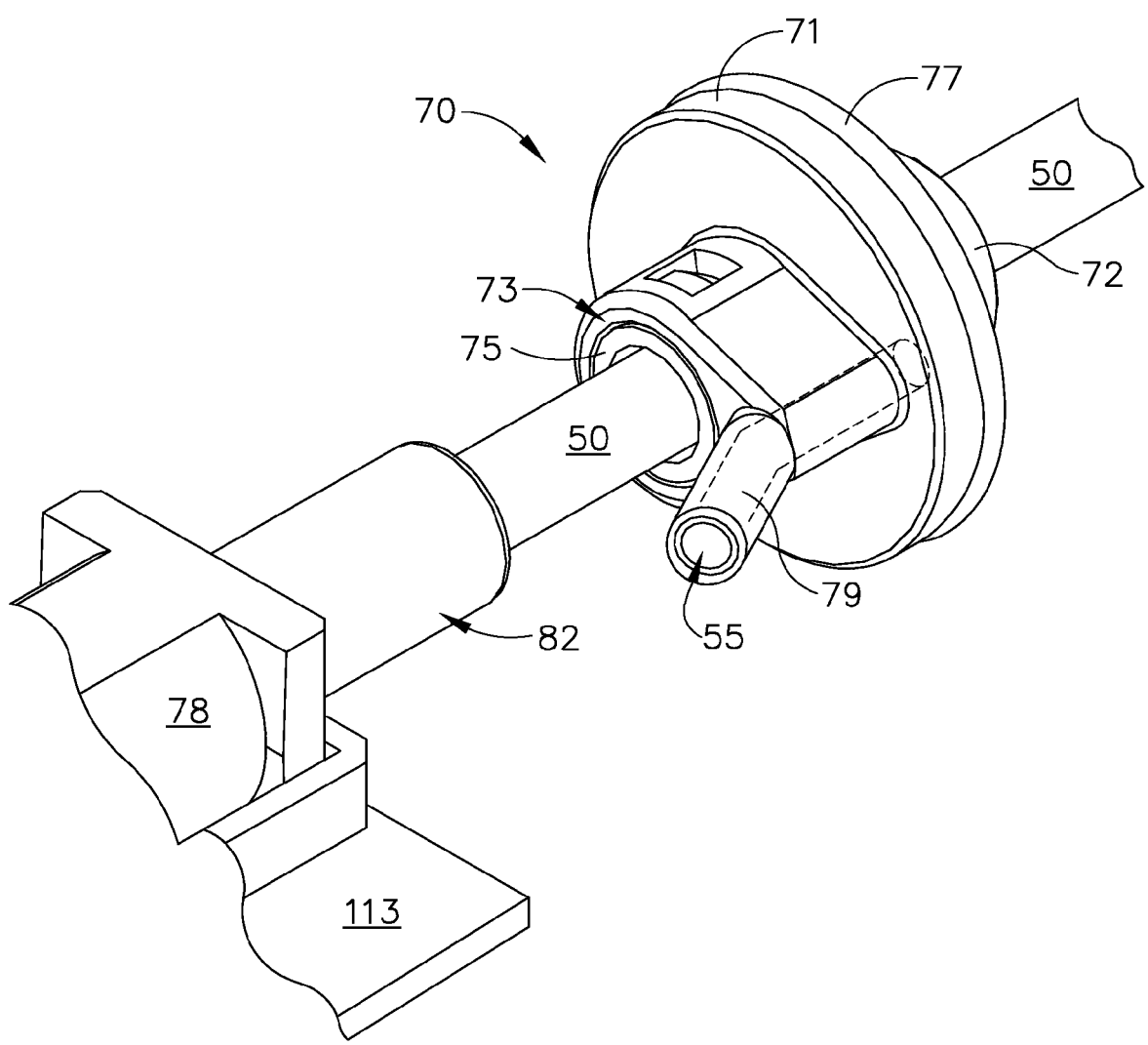
FIG. 9 is a partial perspective view of a vacuum manifold system FIG. 8.

FIG. 8 shows a perspective view of a proximal portion of probe (105) with top cover (114) removed. In this view, bottom cover (116) and can be seen rotatably supporting cutter (50), cutter rotation and translation mechanism (80), vacuum manifold (70), and central thumbwheel (60) at various points such as at a first saddle (124) and a second saddle (125). FIG. 9 shows vacuum manifold (70). Attachment of top cover (114) secures these components (50, 80, 70, 60) between top cover (114), proximal base (113), and bottom cover (116). These components (50, 80, 70, 60) will be described in greater detail below.

In the present example, central thumbwheel (60) does not engage with any portion of holster (205) when probe (105) is releasably attached to holster (205). A tissue sample holder (140) is removably attached to a proximal end of probe (105) for the reception of severed tissue samples therein. Probe (105) is configured for manual insertion into a patient, or can be attached to a stereotactic table or other motorized device for penetration into tissue. A level (199) such as a glass tube with a bubble can be located on top of body portion (112) to indicate when the biopsy device (100) is level. Of course, as with any other components described herein, level (199) may be varied, substituted, supplemented, or omitted as desired.

1. Exemplary Needle

In the present example and as shown in FIG. 6, needle portion (10) extends distally from probe (105), and comprises a hollow outer cannula (12) that defines a cannula lumen (20) and a vacuum lumen (40). A blunt tip (14) is located at a distal end of needle portion (10) and a transverse tissue receiving aperture (16) is located proximally from tip (14). A tissue stop (26) is provided on the proximal side of tip (14). By way of example only, cannula (12) may be introduced into a patient's breast by inserting cannula (12) through a separate cannula (not shown) that has a tissue piercing tip and an aperture that is configured to align with tissue receiving aperture (16) of outer cannula (12). In alternate embodiments, blunt tip (14) may be replaced with a tissue piercing tip (not shown). Such a tissue piercing tip may be configured to penetrate tissue without requiring a high amount of force, and without requiring an opening to be preformed in the tissue prior to insertion of the needle portion (10). One suitable configuration for a tissue piercing tip is disclosed in U.S. Pub. No. 2008/0195066, entitled "Revolving Tissue Sample Holder For Biopsy Device," published Aug. 14, 2008, the disclosure of which is incorporated by reference herein. Other suitable configurations for a tissue piercing tip are disclosed in U.S. Non-Provisional patent application Ser. No. 12/038,359, entitled "Needle Tip for Biopsy Device," filed Feb. 27, 2008, the disclosure of which is incorporated by reference herein. Of course, other suitable configurations for a blunt tip (14) or tissue piercing tip will be apparent to those of ordinary skill in the art in view of the teachings herein.

Transverse tissue receiving aperture (16) is configured to receive tissue drawn within, and cannula (12) has a floor or wall (30) opposite to tissue receiving aperture (16). Wall (30) separates cannula lumen (20) and vacuum lumen (40). A plurality of openings (32) may be formed through wall (30) and provide fluid communication between cannula lumen (20) and vacuum lumen (40). Various ways in which vacuum, saline, atmospheric air, and/or pressurized air, etc., may be communicated through openings (32) will be described in greater detail below. In some versions, wall (30) extends a substantial amount of the length of needle portion (10). In some other versions, wall (30) proximally extends just past the proximal transverse edge of aperture (16). For instance, cannula lumen 20 may be sized and configured such that, with a cutter (50) disposed therein, a gap exists between the exterior of cutter (50) and at least a portion of the interior of cannula (12). Such a gap may define vacuum lumen (40) along part of the length of cannula (12), proximal to the proximal end of wall (30). Still other ways in which a vacuum lumen (40) may be provided will be apparent to those of ordinary skill in the art in view of the teachings herein.

In some versions, a plurality of external openings (not shown) are formed in cannula (12) and are in fluid communication with vacuum lumen (40). Examples of such external openings are disclosed in U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings are merely optional.

As noted above, needle portion (10) extends from a distal end of body portion (112) of probe (105), and rotates around the longitudinal axis defined by needle portion (10). As also noted above, needle orientation indicator (65) is fixedly attached to a proximal end of cannula (12), as an integral part thereof, by overmolding. Of course, adhesives or other techniques or structures may be used to secure needle orientation indicator (65) to cannula (12). The attachment of cannula (12) may provide an airtight or vacuum tight seal between the cannula (12) and needle orientation indicator (65). Needle orientation indicator (65) of the present example is located at a distal end of body portion (112), away from the grasping and balance point of biopsy device (100), and if desired, can be rotated by an operator's free hand.

It should be understood that the components, features, configuration, and functionality of needle portion (10)

described above are merely exemplary. Needle portion (10) may be modified, supplemented, or substituted in any suitable way, as desired. Suitable variations of needle portion (10) and methods of using the same will be apparent to those of ordinary skill in the art in view of the teachings herein.

2. Exemplary Cutter

A hollow cutter (50) is rotatably and slidably movable within cannula lumen (20) of cannula (12), and extends proximally therefrom through body portion (112) of probe (105) to operatively communicate with tissue sample holder (140). Cutter has a sharp distal cutting end (51) to sever tissue. Cutter (50) defines a cutter lumen (52) that is configured communicate fluid and tissue that is severed by cutting end (51) into tissue sample holder (140) as will be described in greater detail below. As will also be described in greater detail below, cutter (50) is configured to both rotate and translate longitudinally within cannula lumen (20) as cutting end (51) cuts tissue. In particular, cutter (50) is configured to sever a biopsy sample from tissue drawn into tissue receiving aperture (16) of outer cannula (12) and to guide or communicate the sample through cutter lumen (52) into tissue sample holder (140). Merely illustrative examples of such severing and proximal communication are described in U.S. Pat. No. 5,526,822, the disclosure of which is incorporated by reference herein, though any other suitable structures or techniques may be used for severing and/or communicating tissue samples within a biopsy system (2).

Cutter (50) may be subject to various treatments or configurations in order to facilitate distal to proximal transmission of tissue samples through cutter lumen (52). For instance, examples of such treatments and configurations are disclosed in U.S. Pub. No. 2008/0195066, entitled "Revolving Tissue Sample Holder For Biopsy Device," published Aug. 14, 2008, the disclosure of which is incorporated by reference herein. Still other suitable variations of cutter (50) will be apparent to those of ordinary skill in the art in view of the teachings herein.

3. Exemplary Thumbwheel

As noted above, needle portion (10) and needle orientation indicator (65) may be operatively rotated using central thumbwheel (60). This rotational movement is around the longitudinal axis defined by needle portion (10). As shown in the exploded view of FIGS. 3-7, needle portion (10) is fixedly attached to needle orientation indicator (65), and thumbwheel (60) is spaced proximally thereto by a hollow sleeve portion (63) that attaches to needle orientation indicator (65) and central thumbwheel (60) with a fluid tight connection. Central thumbwheel (60) has a proximal knob (61) configured with engagement teeth (62) around a periphery thereof to enhance engagement with the operator's finger or thumb. In some versions, engagement teeth (62) can be gear teeth, or may take a variety of other configurations. Hollow sleeve portion (63) extends distally from knob (61) and defines a hollow sleeve lumen (69). An external flange (64) extends in a raised ring around hollow sleeve portion (63) and is disposed a slot (118) in bottom cover (116) of probe (105) (FIG. 6), which permits rotation of sleeve portion (63) while restricting longitudinal movement of sleeve portion (63). A distal keyed end (66) of hollow sleeve portion (63) is configured to attach to both needle portion (10) and needle orientation indicator (65) to create a fluid tight assembly (10, 60, 65) that can be rotated with thumbwheel (60).

The assembly of thumbwheel (60), needle orientation indicator (65), and needle portion (10) brings hollow sleeve lumen (69) into fluid communication with cannula lumen (20) and vacuum lumen (40). In particular, with cutter (50) disposed in hollow sleeve lumen (69) in addition to being disposed in cannula lumen (20), the exterior of cutter (50) and the interior of sleeve lumen (69) may define a lumen that corresponds with vacuum lumen (69) of cannula (12). In some versions, the fluid tight assembly (10, 60, 65) can include an adhesive (not shown) or a weld (not shown) to join needle orientation indicator (66) and needle portion (10) with thumbwheel (60). In other versions, the fluid tight assembly can include a mechanical fastening with a seal. Mechanical fastenings may include but are not limited to a snap coupling, a bayonet coupling, a screw thread, or any other mechanical fastening. Such fastening mechanisms may also include sealing devices such as o-rings, etc.

As shown in FIG. 6, thumbwheel (60) rotatably mounts within body portion (112), with thumbwheel (60) extending through opening (115) in top cover (114) and through opening (117) in bottom cover (116). As shown in FIG. 3, knob (61) of thumbwheel (60) is configured to be received in a recess (204) of holster (205). The recess (204) is configured to receive knob (61) of thumbwheel (60) without any contact therebetween to provide free and unhindered rotation of thumbwheel (60). However, as will be described in greater detail below with respect to other versions, thumbwheel (60) may have a variety of other relationships with components of holster (205).

Thumbwheel (60) of the present example also includes a recessed bore (67) extending into a proximal face of the knob (61), with an internal diameter larger than the diameter of hollow sleeve lumen (69). Recessed bore (67) extends distally past knob (61) to define a shoulder (68). Recessed bore (67) is in open communication with hollow sleeve lumen (69) and is configured to receive and retain a vacuum manifold (70) within, as will be described in greater detail below.

It should be understood that the components, features, configuration, and functionality of needle thumbwheel (60) and associated components described above are merely exemplary. Thumbwheel (60) and associated components may be modified, supplemented, or substituted in any suitable way, as desired. Suitable variations of thumbwheel (60) and associated components and methods of using the same will be apparent to those of ordinary skill in the art in view of the teachings herein.

4. Exemplary Vacuum Manifold

As shown in FIGS. 3-9, an exemplary vacuum manifold (70) is configured to be rotatably received within recessed bore (67) of central thumbwheel (60). Vacuum manifold (70) remains stationary within body portion (112), creates a rotating airtight seal with recessed bore (67) of thumbwheel (60), and creates a dynamic fluid seal with rotating and translating cutter (50). The dynamic fluid seal is configured to maintain fluid integrity when cutter (50) is stationary, when cutter (50) is translating longitudinally relative to needle manifold (80), and/or when cuter (50) rotates about the longitudinal axis. Vacuum manifold (70) also maintains a fluid seal with thumbwheel (60), even as thumbwheel (60) rotates about vacuum manifold (70).

Figure 5:
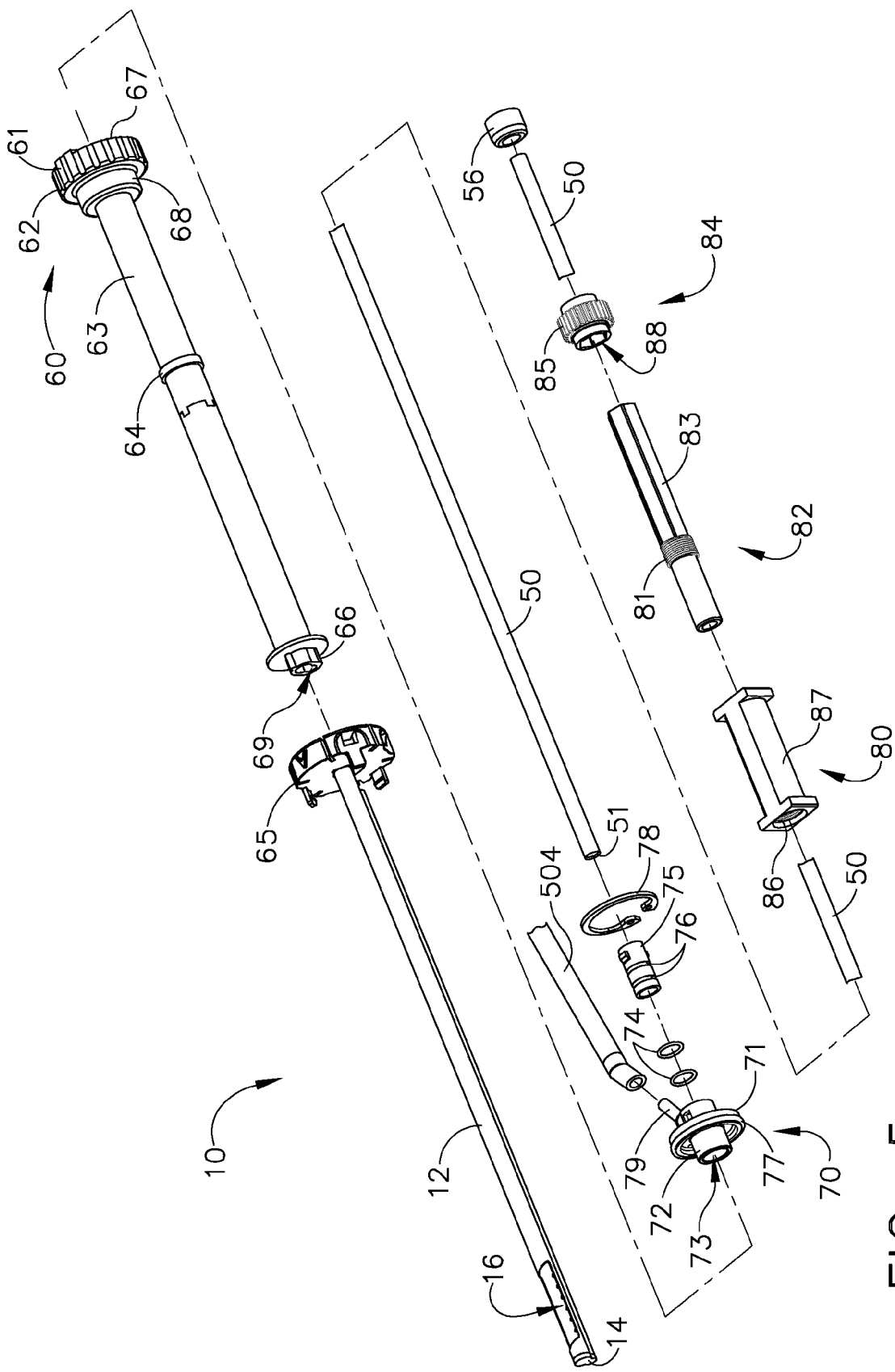
FIG. 5 is an exploded view of the needle and a cutter assemblies of the probe of FIG. 2.

As shown in FIGS. 5, 8, and 9, vacuum manifold (70) of the present example comprises a wheel shaped manifold ring (71) with a manifold sleeve (72) extending proximally and distally through manifold ring (71). A manifold lumen (73) extends longitudinally through a center of manifold sleeve (72) and is configured to receive a cylindrical shaped cutter seal (75). Cutter seal (75) can be formed from an elastomeric seal material and can have at least one inner surface configured to form a dynamic seal with cutter (50). An o-ring (74) can be placed within each of the one or more grooves (76) of cutter seal (75) to form a static seal with manifold lumen (73). O-rings (74) can also provide an inward pinching bias to ensure that cutter seal (75) maintains a dynamic seal with cutter (50). A large o-ring seal (77) is provided to form a rotating seal between manifold ring (71) of vacuum manifold (70) and recessed bore (67) of the central thumbwheel (60). An internal snap ring (78) or other type of fastening structure can retain non-moving vacuum manifold (70) within recessed bore (67) of rotatable central thumbwheel (60).

A vacuum port (79) enters a proximal side of central thumbwheel (60) and contains a vacuum passage (55) connecting to a distal side of central thumbwheel (60) to communicate with recessed bore (67) of the central thumbwheel (60) for the transfer of vacuum or fluids therebetween. Vacuum cannula (79) is connected to a distal end of tube (504) to form an unbroken line of communication (fluids and/or vacuum, etc.) between vacuum control module (500), tube (504), vacuum passage (55), recessed bore (67), hollow sleeve lumen (69), and vacuum lumen (40) of needle portion (10). If desired, a vacuum control valve may be operatively coupled to tube (504) to control when vacuum or fluids are applied thereto. For instance, such a vacuum control valve may be located in vacuum control module (500) or elsewhere. Suitable components and methods relating to communication of vacuum and fluids, as may be implemented in biopsy system (2), are described in U.S. Pub. No. 2008/0195066, entitled "Revolving Tissue Sample Holder For Biopsy Device," published Aug. 14, 2008, the disclosure of which is incorporated by reference herein.

It should be understood that the components, features, configuration, and functionality of vacuum manifold (70) described above are merely exemplary. Vacuum manifold (70) may be modified, supplemented, or substituted in any suitable way, as desired. Suitable variations of vacuum manifold (70) and methods of using the same will be apparent to those of ordinary skill in the art in view of the teachings herein.

5. Exemplary Cutter Rotation and Translation Mechanism

In the present example, and as shown in FIGS. 4, 5, 7-8, and 10, body portion (112) of probe (105) comprises a cutter rotation and translation mechanism (80) to rotate and translate cutter (50). Cutter rotation and translation mechanism (80) comprises a sleeve (82) fixed to cutter (50) with an external threaded portion (81) and a hexagonal drive portion (83). External threaded portion (81) is configured to be in threaded engagement with one or more internal threads (86) within a drive nut (87), and hexagonal drive portion (83) is configured to be in sliding and driving engagement with a hexagonal drive opening (88) within a drive member (84). Drive member (84) further comprises an external drive gear (85) configured to be rotated by an intermediate driven gear (238) of holster (205) to drive cutter rotation and translation mechanism (80).

As shown in FIG. 7, drive nut (87) is engaged with external threaded portion (81) of sleeve (82), and drive member (84) is slidably received on hexagonal drive portion (83) of sleeve (82). Drive nut (87) is securably received within base (113). Drive member (84) is rotatably received in a transverse slot (119) between top cover (114) and base (113), with a portion of external drive gear (85) being exposed through transverse slot (119). External drive gear (85) is configured to drivably engage with an intermediate driven gear (238) of holster (205) when probe (105) is coupled with holster (205). As intermediate driven gear (238) rotates in holster (205), the driving engagement rotates external drive gear (85), which rotates hexagonal drive portion (83) of sleeve (82), thereby rotating cutter (50). As cutter (50) and sleeve (82) are rotated by drive member (84), the threaded engagement between fixed drive nut (87) and external threaded portion (81) of the sleeve (82) translates cutter (50) and sleeve (82) longitudinally. Depending on the direction of rotation of drive member (84), cutter (50) and sleeve (82) translate either proximally or distally along the longitudinal axis. Thus, cutter rotation and translation mechanism (80) simultaneously rotates and translates cutter (50) in response to rotation of drive member (84).

It will be appreciated in view of the teachings herein that cutter rotation and translation mechanism (80) described above is merely exemplary, and that translation and/or rotation of cutter (50) may alternatively be provided in various other ways. For instance, probe (105) may include a motor or other device, such that probe (105) lacks exposed external drive gear (85). It should also be understood that cutter rotation and translation mechanism (80) may be constructed and used in accordance with any of the teachings of U.S. Pub. No. 2008/0195066, entitled "Revolving Tissue Sample Holder For Biopsy Device," published Aug. 14, 2008, the disclosure of which is incorporated by reference herein. Alternatively, any suitable structure other than exposed external drive gear (85) e.g., a rack, etc. may be used to receive communication of motion or energy from some other component, in order to rotate and/or translate cutter (50). Furthermore, cutter rotation and translation mechanism (120) may be configured such that more than one external drive gear (85) is present (e.g., one external drive gear (85) for providing translation motion, and another external drive gear (85) for providing rotation motion, etc.). In other merely illustrative alternatives, translation and/or rotation of cutter (50) may be performed at least in part by pneumatic actuators not shown, pneumatic motors not shown, or a variety of other components. Furthermore, it will be appreciated that pneumatic components may be combined with other mechanical components and/or electromechanical components in order to translate and/or rotate cutter (50). Still other suitable variations of cutter rotation and translation mechanism (80) and methods of using the same will be apparent to those of ordinary skill in the art in view of the teachings herein.

6. Exemplary Tissue Sample Holder and Manifold

Figure 10:
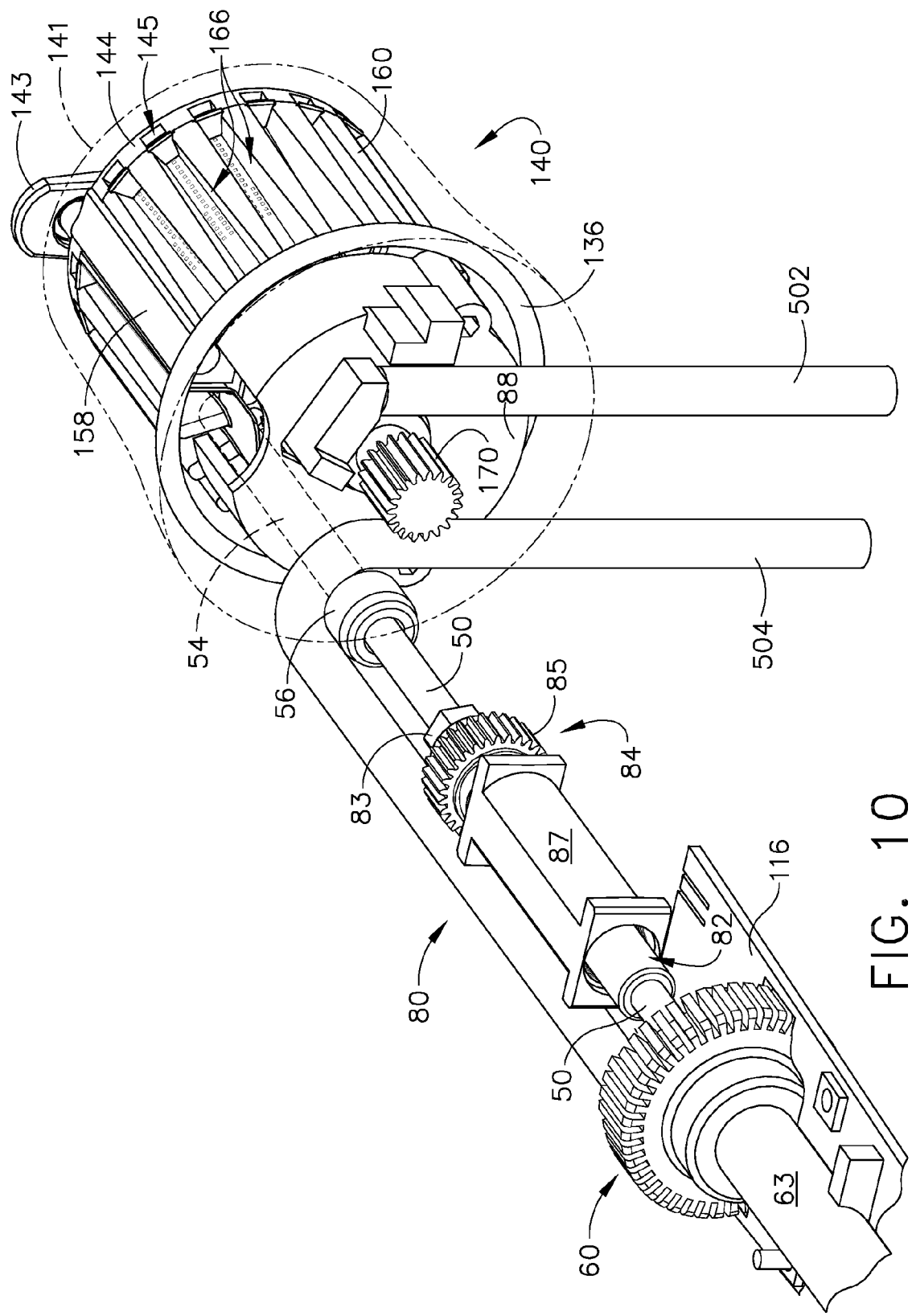
FIG. 10 is a partial perspective view showing a tissue sample holder with a cover in dashed lines and engagement with the cutter drive system of FIG. 8.

As shown in FIGS. 3-4 and 10, proximal base (113) further comprises a light pipe (188) mounted thereto. Light pipe (188) is constructed from a transparent or translucent material and is configured to be illuminated from within by a light source (not shown). Light pipe (188) is located adjacent to a tissue sample holder (140) and can conduct light thereto. An axial vacuum tube (502) is coupled with light pipe (188) and is thereby placed in fluid communication with tissue sample holder (140) by a passage (189) formed through light pipe (188). Of course, light pipe (188) need not be transparent or translucent. By way of example only, light pipe (188) may instead be formed of an opaque plastic or any other material(s) having any suitable properties.

Proximal base (113) further defines tissue sample passage (54), through which the proximal end of cutter (50) is disposed (FIG. 4). A seal (56) is provided at the distal interface of cutter (50) and tissue sample passage (54), to prevent escape of vacuum or fluid between the outer surface of cutter (50) and the tissue sample passage (54) while permitting cutter (50) to rotate and translate relative to seal (56). Tissue sample passage (54) is sized such that, as cutter (50) translates during use of biopsy device (100), the proximal end of cutter (50) remains within tissue sample passage (54) and seal (56) maintains a dynamic seal therewith. Tissue sample passage (54) is thus in sealed fluid communication with cutter lumen (52). Of course, any other suitable structures or configurations may be used. In the present example, tissue sample passage (54) extends proximally from seal (56) to a proximal end of proximal base (113), and is also configured to receive and pass tissue samples emerging from the proximal end of cutter (50). Tissue samples emerge from tissue sample passage (54) and exit into tissue sample holder (140).

As shown in FIGS. 2-4, 8, and 10, tissue sample holder (140) of the present example is located at a proximal end of probe (105) and is configured to receive a plurality of severed tissue samples within as they exit from tissue sample passage (54). Tissue sample holder (140) is further configured to store each sample individually, and the stored samples can be removed from the exemplary tissue sample holder (140) for study. Tissue sample holder (140) of the present example comprises a rotatable manifold (144). Manifold (144) is configured to removably attach to and rotate around a longitudinal shaft (147) (FIGS. 3 and 4) to successively align tissue sample chambers (146) with tissue sample passage (54) for the reception of tissue samples therefrom, as will be described in greater detail below. Manifold (144) has a paddlewheel like configuration, and has a plurality of outwardly extending paddles (not shown). The paddles are radially spaced about manifold (144), and extend longitudinally.

Manifold (144) further comprises a plurality of inner openings (not shown) and a corresponding set of rear openings (145). The inner openings are radially spaced about the distal face of manifold (144), facing light pipe (188), and extend longitudinally through a portion of manifold (144). Each inner opening is discrete from the other inner openings, and communicates with a respective internal passage (144) that also communicates with an associated rear opening (145). The inner openings of manifold (144) are positioned to successively align with passage (189) formed through light pipe (188). Given this, and the communication of each inner passage of manifold (144) with a corresponding rear opening (145), those of ordinary skill in the art will recognize in view of the teachings herein that rear openings (145) may be successively placed in fluid communication with tube (502) as manifold (144) is rotated by shaft (147). Furthermore, as each inner opening of manifold (144) is indexed to passage (189), a corresponding tissue sample chamber (166) (that corresponds with the associated rear opening (145)) is also concomitantly indexed to tissue sample passage (54).

As shown in FIG. 10, one or more tissue sample trays (160) are configured to removably mount over the plurality of outwardly extending paddles of manifold (144). Tissue sample trays (160) define a plurality of tissue sample chambers (166) that correspond with gaps defined between the paddles of manifold (144). The outwardly extending paddles of manifold (144) are thus covered by tissue sample trays (160). Tissue sample trays (160) are configured to receive a severed tissue sample within each tissue sample chamber (166), and are further configured for removal from manifold (144) so that one or more trays (160) of tissue samples may be sent to pathology. Replacement tissue sample trays (160) may be provided to replace trays (160) removed during a procedure. Tissue sample trays (160) may include markings or other indicia.

Tissue sample trays (160) are configured and positioned to provide fluid communication from rear openings (145) to tissue sample passage (54). In particular, such fluid communication may be provided through whichever tissue sample chamber (166) is indexed to tissue sample passage (54). It will therefore be appreciated in view of the teachings herein that tissue sample passage (54) (and hence, cutter lumen (52)) may be placed in fluid communication with tube (502) via whichever tissue sample chamber (166) and associated rear opening (145) is indexed to tissue sample passage (54). By way of example only, a vacuum may be communicated through tube (502) to draw a severed tissue sample through cutter lumen (52) and into whichever tissue sample chamber (166) is indexed to tissue sample passage (54).

Manifold (144) of the present example is thus configured to rotate relative to proximal base (113), to align one tissue sample chamber (166) with tissue sample passage (54). Vacuum may be communicated to tissue sample holder (140) from tube (502). When a tissue sample has been severed by cutting end (51) of cutter (50) and a vacuum is applied to tissue sample holder (140) by tube (502), the severed tissue sample is drawn down cutter lumen (52), into the tissue sample passage (54), and is deposited into the aligned tissue sample chamber (166).

Tissue sample holder (140) further comprises a removable cup (141) that surrounds a rotatable manifold (144). Removable cup (141) is releasably attached to base (113) via a coupling such as a bayonet coupling (134). An O-ring or cup seal (136) can be placed between base (113) and the removable cup (141) to create a vacuum or fluid seal therewith. Rotation of removable cup (141) disengages bayonet coupling (134), allowing cup (141) to be removed (not shown). Removal of cup (141) exposes manifold (144) and tissue sample trays (160) (FIG. 10). Cup (141) is also formed of a transparent material in the present example, enabling the user to visually inspect tissue samples in tissue sample holder (140) while tissue sample holder (140) is still coupled with proximal base (113). Light pipe (188) can provide illumination for the tissue sample holder (140). Of course, cup (141) may alternatively have any other suitable properties.

As noted above, manifold (144) is configured to removably attach to and be rotated by shaft (147). As shown in FIGS. 3-4, shaft (147) is rotatably received within base (113) and rotates about an axis parallel to the longitudinal axis defined by cutter lumen (52). The distal end of shaft (147) has a unitary gear (170), which is configured to drive or rotate manifold (144). Shaft (147) may rotate manifold (144) by a keyed engagement such as a blade or woodruff key extending from a round portion of the shaft (147). As will be described in greater detail below, gear (170) is configured to mesh with a drive gear (251) of holster (205), such that gear (251) may be used to impart rotation to gear (170). Such rotation may be used to selectively (e.g., consecutively) align tissue sample chambers (166) with tissue sample passage (54), to successively collect a discrete tissue sample in each chamber (166) during use of biopsy device (100).

As shown in FIG. 10, tissue sample holder (140) of the present example has a longitudinal passage (158) formed through manifold (144). Passage (158) of this example is a hollow rectangular tube structure extending longitudinally, completely through manifold (144), and is offset from but parallel with the central axis defined by manifold (144). Like chambers (166), passage (158) is configured to be selectively aligned with tissue sample passage (54) and to form a continuous passageway through tissue sample passage (54), and through cutter lumen (52). Passage (158) of the present example is configured to permit instruments and/or liquids, other materials, etc., to be passed through manifold (144) and through tissue sample passage (54). For instance, passage (158) may be used to insert an instrument for deploying one or more markers at a biopsy site, via tissue sample passage (54) and via cutter lumen (52), out through aperture (16). A merely exemplary marker applier that may be inserted through passage (158) may include the MAMMOMARK biopsy site marker applier, by Ethicon Endo-Surgery, Inc. of Cincinnati, Ohio. Other suitable marker applier devices that may be inserted through passage (158) may include any of those described in U.S. Pat. No. 7,047,063; U.S. Pat. No. 6,996,433; U.S. Pat. No. 6,993,375; or U.S. Pub. No. 2005/

0228311, the disclosure of each of which is incorporated by reference herein. Any of such appliers, including variations of the same, may be introduced through passage (158) to deploy one or more markers at a biopsy site, via aperture (16), while needle portion (10) remains inserted in a patient e.g., shortly after biopsy samples are extracted from the patient, etc. Such marker deployment may be accomplished even while tissue samples reside within tissue sample holder (140), secured to biopsy probe (105). Alternatively, such marker appliers may be inserted directly into tissue sample passage (54) with tissue sample holder (140) being removed from biopsy probe (105).

It should be understood that tissue sample holder (140) and its associated components may be constructed and used in accordance with any of the teachings of U.S. Pub. No. 2008/0195066, entitled "Revolving Tissue Sample Holder For Biopsy Device," published Aug. 14, 2008, the disclosure of which is incorporated by reference herein. By way of example only, probe (105) may include a parking pawl (not shown) to selectively engage gear (170) to prevent rotation of manifold (144) when probe (105) is decoupled from holster (205). As another variation, tissue sample holder (140) may be constructed and used in accordance with any of the teachings of U.S. Non-Provisional patent application Ser. No. [FBT DOCKET NO. 0021680.END6471USNP], entitled "BIOPSY DEVICE WITH DISCRETE TISSUE CHAMBERS," filed on even date herewith, the disclosure of which is incorporated by reference herein. Still other suitable variations of tissue sample holder (140), its associated components, and methods of using the same will be apparent to those of ordinary skill in the art in view of the teachings herein.

B. Exemplary Holster

Figure 11:
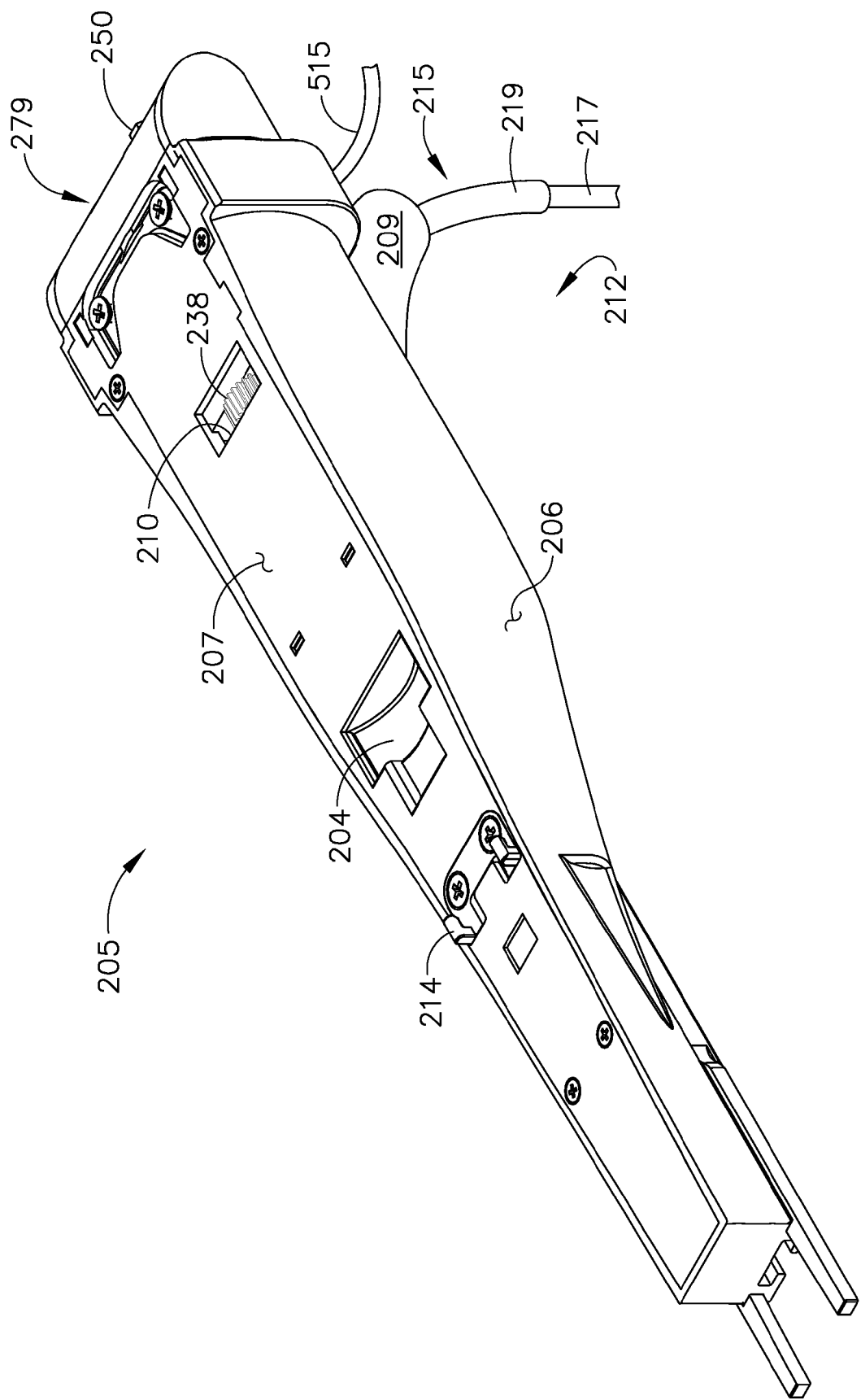
FIG. 11 is a perspective view of the holster of FIG. 2.
Figure 12:
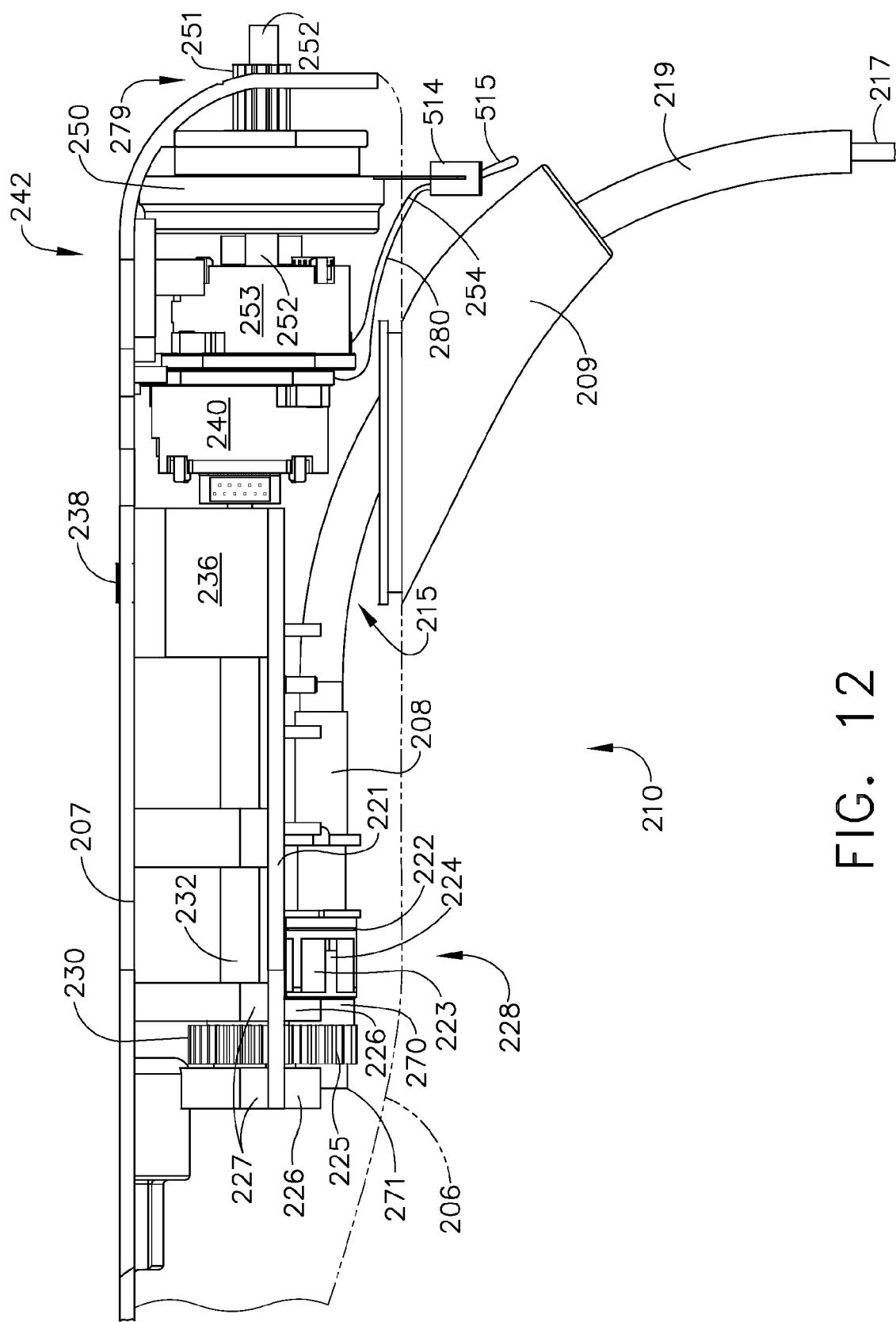
FIG. 12 is a side view of the holster of FIG. 2, with a dashed outline to indicate a lower cover of the holster and showing a cutter drive system and a tissue sample holder drive system.

As shown in FIGS. 3 and 11, holster (205) of the present example comprises a body (212) having a top housing member (207), through which a portion of an intermediate driven gear (238) is exposed, and a bottom housing member (206). Recess (204) is provided in top housing member (207) to receive thumbwheel (60) within without interference or contact therewith when probe (105) is coupled with holster (205). A plurality of hook members (214) extend from top housing member (207) for selectively securing probe (105) to holster (205), though other structures or techniques may be used. Holster (205) of this embodiment further comprises a cutter drive mechanism (210) and a tissue holder rotation mechanism (240). Each of these merely exemplary components will be described in greater detail below. Holster (205) of the present example is configured to be coupled with a biopsy probe (105), such as biopsy probe (105) described above, to provide a biopsy device (100). In addition, holster (205) is configured to be handheld, such that biopsy device (105) may be manipulated and operated by a single hand of a user (e.g., using ultrasound guidance, etc.). However, it will be appreciated in view of the disclosure herein that holster (205) may be used in a variety of other settings and combinations.

1. Exemplary Cutter Drive Mechanism

As shown in FIGS. 3 and 11-14, cutter drive mechanism (210) of the present example comprises a drive cable (215) having an inner wire cable (217) rotatably encased in a sheath (219). Drive cable (215) extends between holster (205) and the vacuum control module (500). A motor (530) is located within vacuum control module (500) and is operably coupled to a proximal end of the drive cable (215) (FIG. 1) to rotate inner wire cable (217) within the non-rotating sheath (219). By way of example only, motor (530) may be provided in accordance with, and incorporated with vacuum control module (500) in accordance with, the teachings of U.S. Non-Provisional patent application Ser. No. [FBT DOCKET NO. 0021680.END6466USNP], entitled "CONTROL MODULE INTERFACE," filed on even date herewith, the disclosure of which is incorporated by reference herein.

Drive cable (215) enters into bottom housing member (206) through a strain relief (209). A distal end connector (208) is crimped or attached to a distal end of non-rotating sheath (219) for attachment to the holster (205). End connector (208) is captured between bottom housing member (206) and a bottom portion of a middle plate (221) of holster (205) to secure drive cable (215) to holster (205). Middle plate (221) is an intermediate bearing plate that mounts into bottom housing member (206) to securely capture the distal end of non-rotating sheath (219) and will be described in more detail below. A distal end of inner wire cable (217) is attached to a cable drive gear (225) by a shock assembly (228). Shock assembly (228) is an energy absorber configured to reduce rotational drive shocks between inner wire cable (217) and cable drive gear (225). Shock assembly (228) comprises a flex end coupling (222) fixedly attached to the inner wire cable (217), and a holster end coupling (224) fixedly attached to the cable drive gear (225). Gaps between flex end coupling (222) and holster end coupling (224) are filled with an elastomeric shock absorber (223) that is captured between flex end coupling (222) and holster end coupling (224). Shock absorber (223) is configured to transmit rotation from inner wire cable (217) to cable drive gear (225) and is also configured to accommodate misalignment between inner wire cable (217) and cable drive gear (225). Shock absorber (223) may also smooth velocity or rotational differences between inner wire cable (217) and cable drive gear (225). Of course, as with other components described herein, shock assembly (228) is merely optional. By way of example only, inner wire cable (217) may be directly connected to cable drive gear (225) if desired.

Cable drive gear (225) is rotatably secured between drive gear saddles (226) extending downward from a distal end of middle plate (221); while opposing drive gear saddles (not shown) extend upward from an inside of bottom housing member (206) such that cable drive gear (225) is supported therebetween. Rotation of inner wire cable (217) rotates cable drive gear (225) in saddles (226).

On a top of middle plate (221), a pair of driven gear saddles (227) extend upwardly from the distal end of middle plate (221) in direct opposition to saddles (226) extending downwardly from middle plate (221). Driven gear saddles (227) rotatably support an idler driven gear (230) therebetween, and are positioned to align idler driven gear (230) directly above cable drive gear (225) and in toothed driving engagement therewith. The driving engagement of idler driven gear (230) with cable drive gear (225) enables idler driven gear (230) to rotate in response to rotation of inner wire cable (217) of drive cable (215).

An idler shaft (232) extends proximally from a center of idler driven gear (230), and has an idler drive gear (234) attached to idler shaft (232) at a location proximally spaced from the driven gear (230). Both idler gear (234) and idler shaft (232) are rotatably received in an idler saddle block (236) extending upwardly from a proximal end of middle plate (221). Idler saddle block (236) is configured to rotatably support inline idler shaft (232) and idler gear (234), as well as an intermediate driven gear (238) located above idler gear (234). As shown, idler gear (234) is in driving engagement with intermediate driven gear (238) and is supported above in a position where a portion of the intermediate driven gear (238) is exposed through an opening (211) (FIG. 11) within top housing member (207).

When top housing member (207) is attached to bottom housing member (206), idler shaft (232), idler gear (234), and intermediate driven gear (238) are rotatably captured between saddle block features extending downward from top housing member (207) to engage with driven gear saddles (227) and idler saddle block (236). With appropriate material selection, the rotating elements of cutter drive mechanism (210) such as idler shaft (232) may be run within saddles (226, 227, 236, etc.). By way of example only, bearings may be provided to support the rotating elements and to reduce friction. These bearings may be of any conventional bearing construction such as ball bearings, roller bearings, or sleeve bearings, and can be provided with or without lubricants. If needed, seals such as oil or grease seals may be provided for use with the bearings to prevent migration of lubricants to unwanted areas. For instance, sleeve bearings may be molded from slick or lubricious materials such as nylons, acetals (delrin), Teflon impregnated polymers, or any other moldable sleeve bearing materials.

Figure 13:
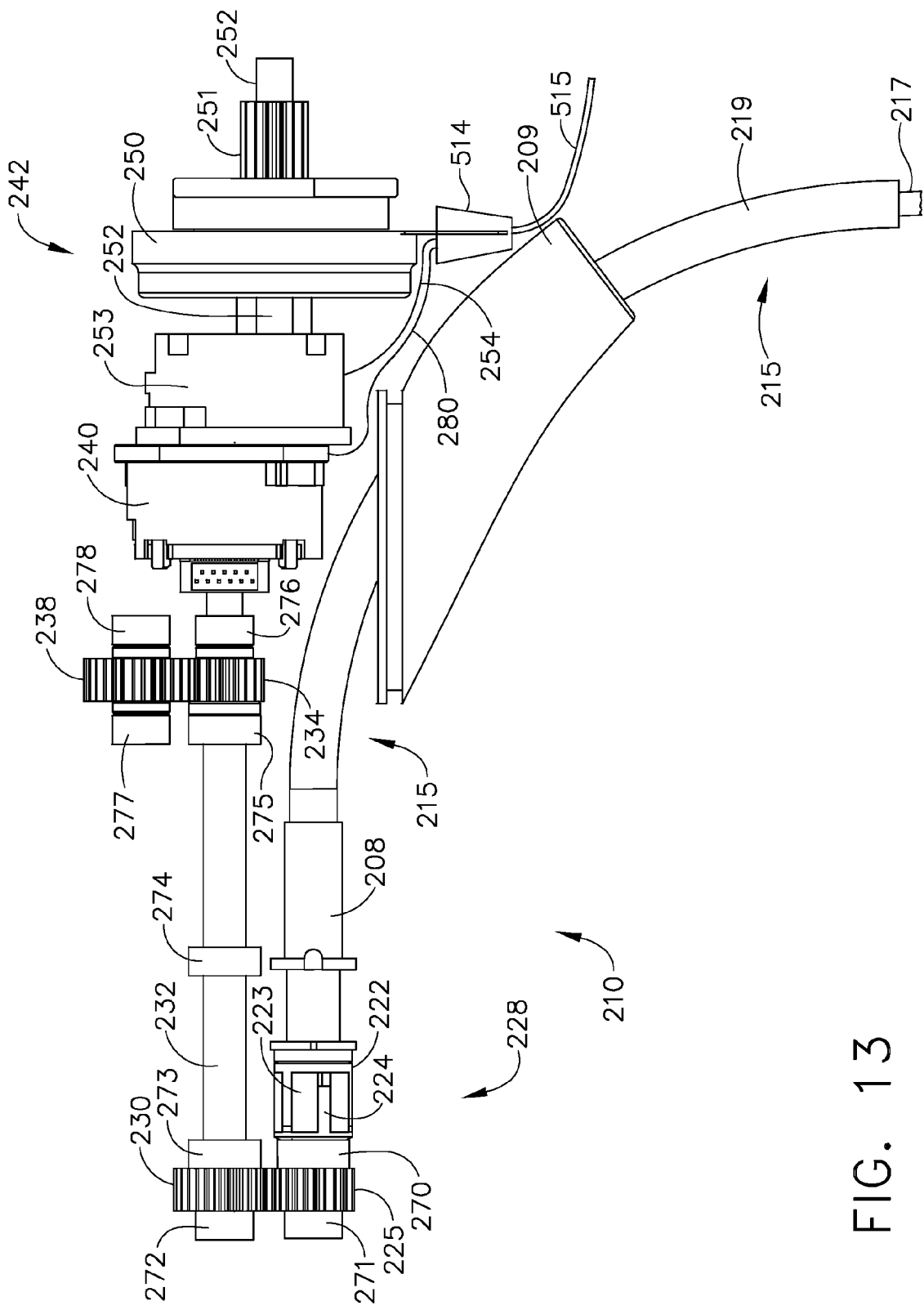
FIG. 13 is a side view of the view of the cutter drive system and tissue sample holder drive system FIG. 12, with an internal support structure removed to show additional components of the cutter drive system.
Figure 14:
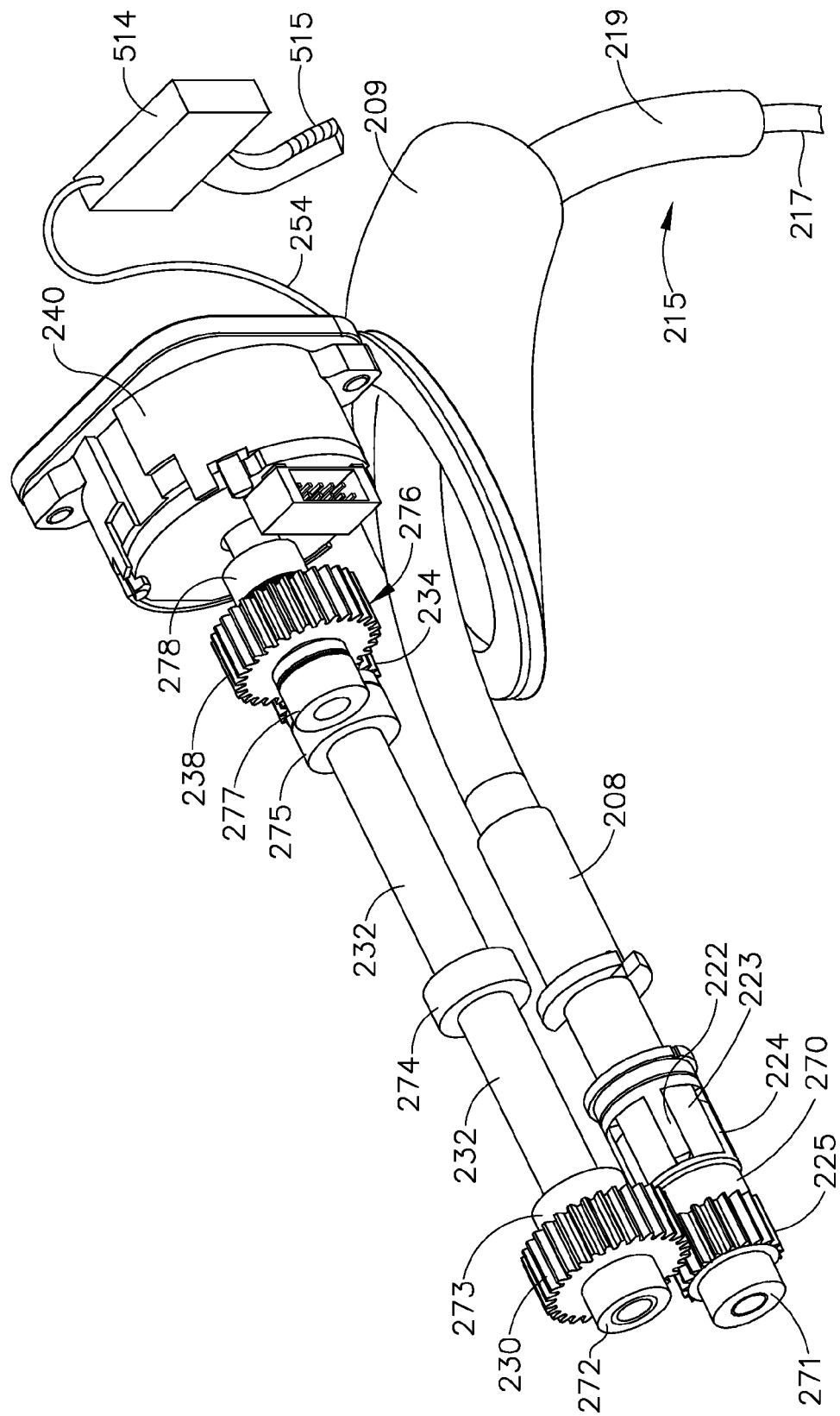
FIG. 14 is a perspective view of the cutter drive system of FIG. 12.

As shown in FIGS. 13-14, cable drive gear (225) may be supported on either side by a first bearing (270) and a second bearing (271). Third bearing (272) and fourth bearing (273) are placed to support idler driven gear (230) on either side; and fifth bearing (274) is placed to support a center of the idler shaft (232). Idler drive gear (234) is supported by sixth bearing (275) and seventh bearing (276); and intermediate driven gear (238) can be supported by eighth bearing (277) and ninth bearing (278).

When biopsy probe (105) attaches to holster (205), external drive gear (85) extending from biopsy probe (105) is brought into driving engagement with intermediate driven gear (238), and cutter drive mechanism (210) is thus operably engaged with cutter rotation and translation mechanism (80) of the biopsy probe (105). It will therefore be appreciated by those of ordinary skill in the art that rotation of inner wire cable (217) of drive cable (215) causes simultaneous rotation and translation of cutter (50) in this example.

Of course, cutter drive mechanism (210) may take a variety of other forms, and may have any number of alternative features, components, configurations, and principles of operation. It should therefore be understood that the above described cutter drive mechanism (210) is merely one example. By way of example only, a motor may be provided in holster (205) for driving gears (238, 85), eliminating drive cable (215). As another merely illustrative example, cutter drive mechanism (210) may be configured in accordance with the teachings of U.S. Pub. No. 2008/0195066, entitled "Revolving Tissue Sample Holder For Biopsy Device," published Aug. 14, 2008, the disclosure of which is incorporated by reference herein. Other suitable features, components, configurations, and principles of operation of a cutter drive mechanism (210) will be apparent to those of ordinary skill in the art in view of the teachings herein.

2. Exemplary Idler Shaft Encoder

In the present example, an encoder assembly (240) mounts to a proximal end of idler shaft (232) and is operably connected to motor (530) via wiring (280) extending between holster (205) and vacuum control module (500). Encoder assembly (240) is secured in holster (205) between top housing member (207) and bottom housing member (206). Wiring (280) extends to a connector (514), to which another wire (254) is connected as described below. An encoder cable (515) extends from connector (514) to vacuum control module (500). Encoder assembly (240) of this example measures rotational movement of idler shaft (232) and may be used to "count" revolutions of idler gear shaft (232), which may be used (e.g., with the thread ratio of threads (81, 86)) to indirectly measure rotation and translation (linear travel) of cutter (50) within probe (105). Gears (225, 230, 234, 238) of the present example are configured to provide a 1.5:1 rotational ratio between wire cable (217, 317) of drive cable (215, 315) and idler shaft (232); and a 1:1 rotational ratio between wire cable (217, 317) of drive cable (215, 315) and the intermediate driven gear (238). Encoder assembly (240) "counts" 1.5 revolutions at idler shaft (232) for every rotation of wire cable (217, 317) of drive cable (215, 315). The rotational and positional information from encoder assembly (240) may be used to determine if idler shaft (332) is rotating, may measure idler shaft (332) speed, may measure rotational position of shaft (332), and/or may be used for homing routines to determine the location of cutter (50) (e.g., longitudinal position) within biopsy device (101). Alternatively, any other suitable use may be made of encoder assembly (240), to the extent that an encoder assembly (240) is included at all.

Homing routines may engage motor (530) to move cutter (50) to a proximal most or a distal most position. Cutter (50) may contact a stop at the proximal most or the distal most position that prevents further movement of cutter (50). With cutter (50) stopped, encoder assembly 240 stops rotating, which informs motor control system (540) that a homing position has been reached, and a counter within motor control system (540) is set to zero. With the counter at set at zero at the "home" position, each revolution of idler shaft (332) may be used to calculate linear and rotational positioning of cutter (50) within biopsy probe (105). By way of example only, each revolution of inner wire cable (217, 317) of drive cable (215, 315) may results in approximately 0.00012 inches of linear translation of cutter (50), and each revolution of inner wire cable (217, 317) rotates idler shaft (232) an amount of 1.5 revolutions. Of course, any other suitable ratios may be used.

3. Exemplary Tissue Holder Rotation Mechanism

As described above, and as shown in FIGS. 3-4 and 10, tissue sample holder (140) on probe (105) contains manifold (144) which is aligned and rotated during the acquisition of consecutive tissue samples. In particular, manifold (144) is rotated to successively index tissue collection chambers (166) to tissue sample passage (54), which is aligned with cutter lumen (52). The rotation and alignment of the manifold (144) may ensure that each severed tissue sample is stored separately in an empty tissue sample chamber (166). In the present example, a tissue holder rotation mechanism (242) is provided within holster (205) to engage with holder gear (170), and to rotate manifold (144) when biopsy probe (105) is attached to holster (205).

Tissue holder rotation mechanism (242) of the present example comprises a piezoelectric motor (250) mounted in holster (205). Piezoelectric motor (250) is a piezo effect stepper motor that is slidably received in bottom housing member (206) of holster (205) and is constrained therein by top housing member (207). Piezoelectric motor (250) may be magnetic resonance compatable and may be configured to operate in the magnetic resonance environment. One suitable motor for piezoelectric motor (250) is a Shinsei piezoelectric motor USR30-B4 or a non-magnetic Shinsei piezoelectric motor such as the USR30-S4N, both available from Shinsei Corporation, 2-1-8 Kasuya Setagaya-ku Tokyo 157-0063 Japan. Piezoelectric motor (250) comprises rotatable shaft (252) extending proximally from motor (250). A holder drive gear (251) is attached to a proximally extending portion of shaft (252) to extend proximally through an opening (279) (FIG. 3) in a proximal end of top housing member (207). A portion of holder drive gear (251) is exposed by opening (279) and is configured to engage with the exposed holder gear (170) on the underside of probe (105) when probe (105) is coupled with holster (205). When probe (105) is coupled with holster (205) to engage holder drive gear (251) with the holder gear (170) and piezoelectric motor (250) is actuated, manifold (144) is rotated within tissue sample holder (140).

An encoder (253) mounts to a distally extending portion of shaft (252) and is used to sense rotational motion or rotational positioning of piezoelectric motor (250), and to indirectly measure movement of manifold (144) within the tissue sample holder (140). A cable or wire (254) extends from encoder (253) to connector (514), to encoder cable (515), and to vacuum control module (500). As noted above, encoder assembly (240) and the idler shaft (232) are also electrically coupled to vacuum control module (500) via wire (280) connecting to connector (514) and encoder cable (515). Encoder cable (515) may extend along sheath (219) and may be secured thereto or therein. Alternatively, encoder cable (515) may be provided as separate from sheath (219). Further still, encoder cable (515) and wires (280, 254) may be eliminated, and electronic communication may be provided wirelessly. As yet another merely illustrative variation, cable (515) and wires (280, 254) may be attached or integrated circumferentially with mechanical cable (215). Of course, encoders (240, 253) may also be omitted altogether if desired.

It should be understood that tissue holder rotation mechanism (242) may be varied in a number of ways. By way of example only, tissue holder rotation mechanism (242) may be modified in accordance with the teachings of U.S. Pub. No. 2008/0195066, entitled "Revolving Tissue Sample Holder For Biopsy Device," published Aug. 14, 2008, the disclosure of which is incorporated by reference herein. As another merely illustrative variation, tissue holder rotation mechanism (242) may be driven by cable (217) or another drive cable that is driven by a remote motor. As yet another merely illustrative variation, tissue holder rotation mechanism (242) may be omitted altogether. For instance, tissue sample holder (140) may be manually rotatable or non-rotatable, if desired. As yet another merely illustrative variation, biopsy probe (100) may be configured in accordance with U.S. Non-Provisional patent application Ser. No. [FBT DOCKET NO. 0021680.END6465USNP], entitled "MECHANICAL TISSUE SAMPLE HOLDER INDEXING DEVICE," filed on even date herewith, the disclosure of which is incorporated by reference herein, and which includes several examples of how manual rotation of tissue sample holder (140) may be provided. Still other suitable features, components, configurations, and principles of operation of a tissue holder rotation mechanism (242) will be apparent to those of ordinary skill in the art in view of the teachings herein.

C. Exemplary Use

In one example of operation, as biopsy probe (105) is attached onto holster (205), such that holder gear (170) on biopsy probe (105) is brought into engagement with holder drive gear (251). A parking pawl (not shown) has held manifold (144) in a first position with a first predetermined chamber (166) aligned with tissue sample passage (54) for the reception of the first biopsy tissue sample within. Once gears (170, 251) are engaged and parking pawl (182) is disengaged, the rotational positioning of manifold (144) is controlled by piezo motor (250). Software or control logic is used to automatically reposition manifold (144) after each tissue sample is received within an empty chamber (166) to move a fresh empty chamber (166) into alignment with the tissue sample passage (54) for the receipt of the next tissue sample therein. Piezo motor (250) may also be commanded to "present" a captured tissue sample to the operator before indexing the next empty chamber to tissue sample passage (54). Examples of such tissue sample presentation are disclosed in U.S. Pub. No. 2008/0195066, entitled "Revolving Tissue Sample Holder For Biopsy Device," published Aug. 14, 2008, the disclosure of which is incorporated by reference herein.

For acquisition of a tissue sample, biopsy device (100) is grasped in a single hand (1000) of the operator or surgeon by grasping biopsy device (100) from the top or in any other suitable fashion. For instance, the fingers of the surgeon's hand (1000) may be curled under the holster (205) with the surgeon's thumb on the top of probe (105). With biopsy device held in the surgeon's hand (1000) in this manner, the thumb of the grasping hand may be lifted from biopsy probe (105) and moved to reach out and access thumbwheel (60) protruding from the top of probe (105). Lateral movement of the surgeon's thumb (of the grasping hand) may rotate thumbwheel (60) and needle portion (10) to orient aperture (16) at a desired angular orientation about the axis defined by cannula (12). Alternately, biopsy device (100) may be mounted to a targeting set, such as any of the devices disclosed in U.S. Non-Provisional patent application Ser. No. [FBT DOCKET NO. 0021680.END6474USNP], entitled "MUTLI-ORIENTATION TARGETING SET FOR MRI BIOPSY DEVICE," filed on even date herewith, the disclosure of which is incorporated by reference herein.

II. Second Exemplary Holster

Figure 15:
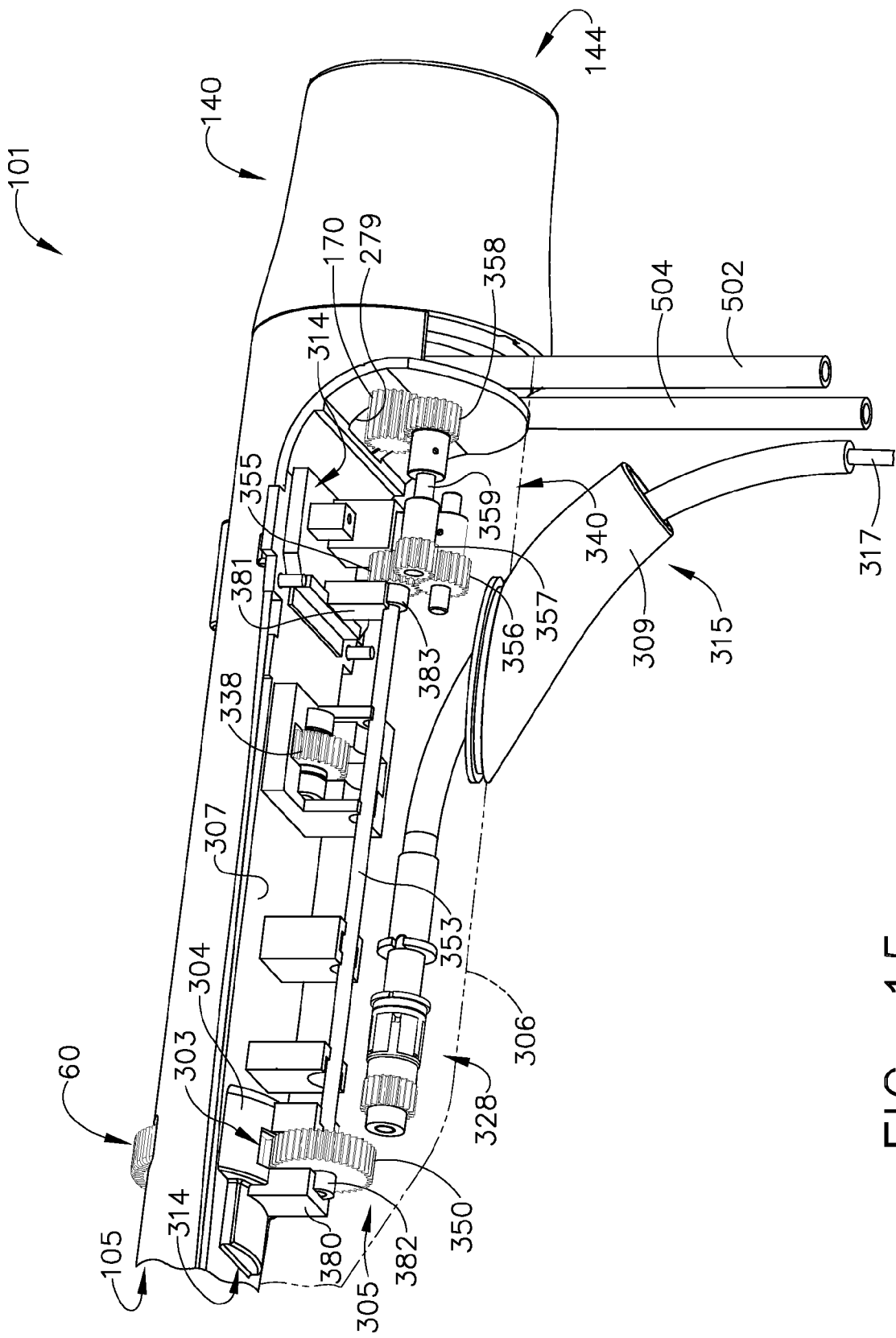
FIG. 15 is a perspective view of an exemplary alternate tissue sample holder drive system linking a central rotation knob a tissue sample holder.
Figure 16:
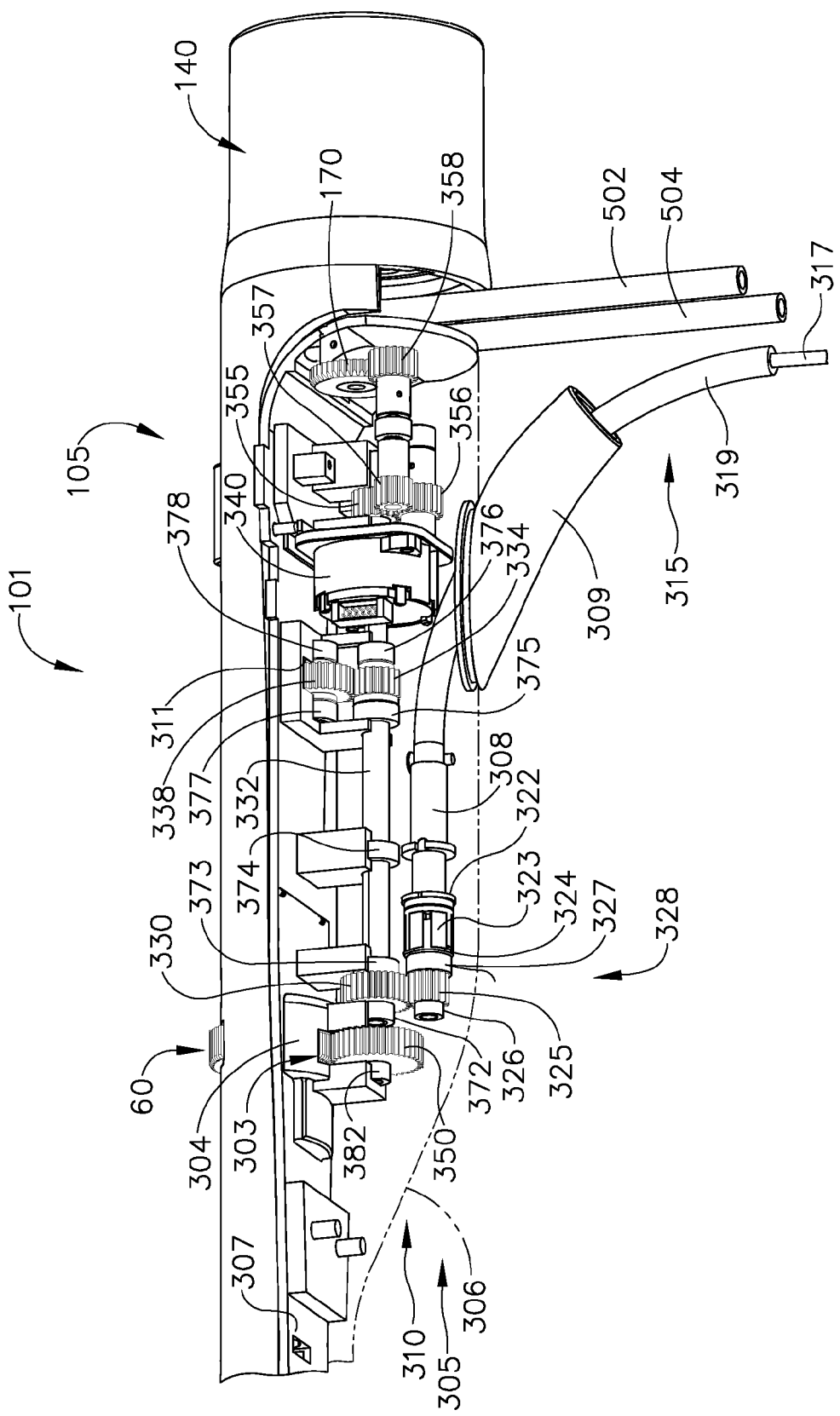
FIG. 16 is a perspective view of the tissue sample holder drive system of FIG. 15, showing the tissue sample holder drive system extending through a cutter drive system.
Figure 17:
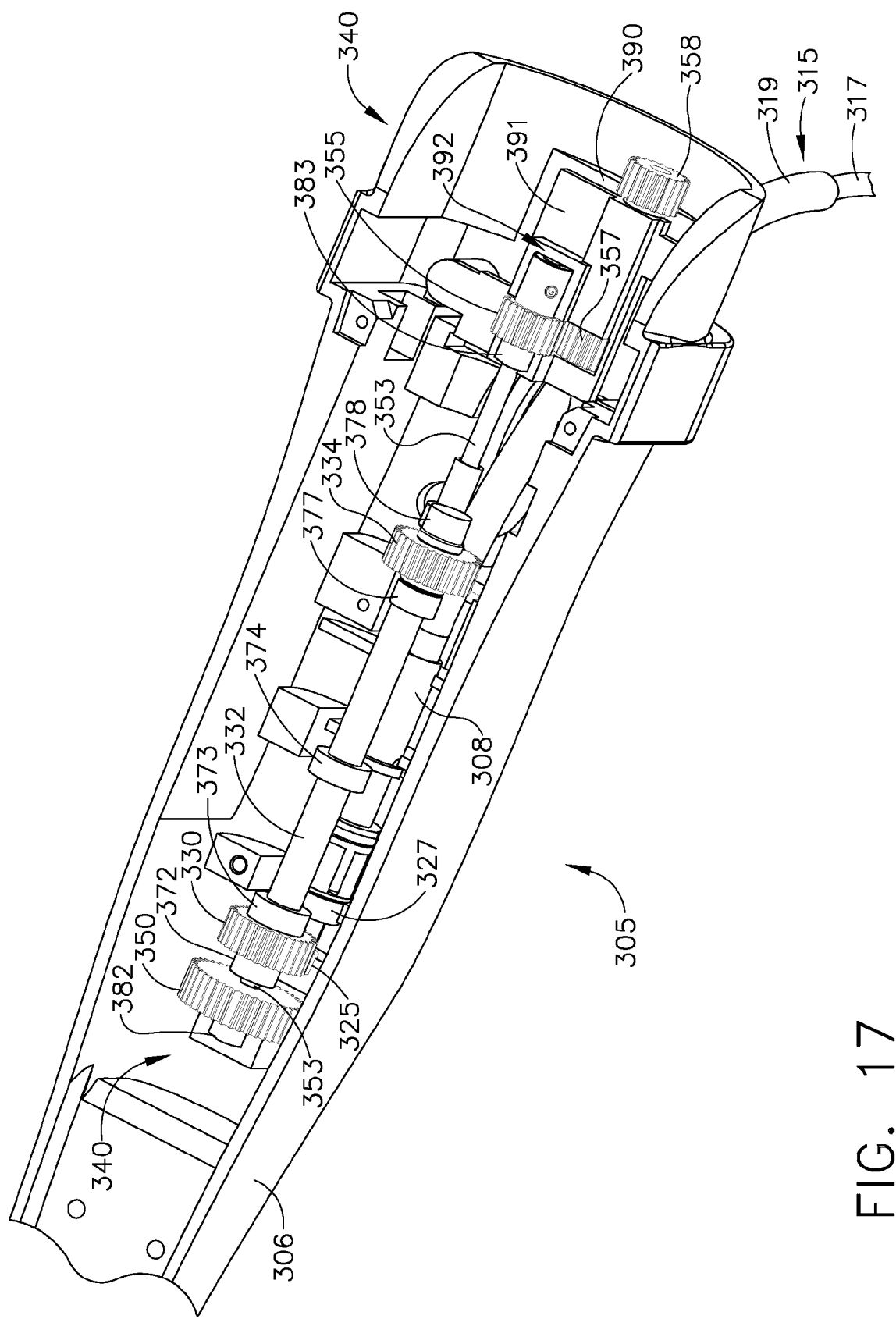
FIG. 17 is a perspective view of the drive systems of FIG. 16, with a top cover of the holster removed to show engagement of the drive systems with the lower cover of a holster.

As shown in FIGS. 15-17, another exemplary biopsy device (101) comprises the above described probe (105) in combination with a different holster (305). The assembly thereof is sized and configured for one handed operation, and is configured for one fingered rotation of the central thumbwheel (60). In FIGS. 15-16, probe (105) and holster (305) are shown releasably assembled together and ready for the acquisition of tissue samples from a patient. Unlike the previously described biopsy device (100), when probe (105) is assembled with holster (305), central thumbwheel (60) of biopsy probe (105) is rotatably coupled to a rotatable manifold such as rotatable manifold (144) (within tissue sample holder (140)) by holster (305). The assembly of probe (105) and holster (305) is thus such that rotation of central thumbwheel (60) rotates the rotatable manifold (144). Disassembly of probe (105) from holster (305) disengages central thumbwheel (60) from rotatable manifold (144).

The rotational linking of central thumbwheel (60) and rotatable manifold (144) ensures that tissue samples are stored within rotating manifold (144) at the same rotational angle as tissue receiving aperture (16) of the needle portion (10). Alternatively, the rotational linking may provide some other direct correlation between the rotational angle of aperture (16) and manifold (144). As noted above, and as will be described in greater detail below, central thumbwheel (60) and rotatable manifold (144) are not linked together within probe (105) in this example, for the linking between thumbwheel (60) and manifold (144) occurs within holster (305) when probe (105) is coupled with holster (305).

As shown in FIGS. 15-17, holster (305) of this example further comprises an exemplary tissue holder rotational mechanism (340) and an exemplary cable driven cutter drive mechanism (310). Holster 305 comprises a top housing member (307) and a bottom housing member (306). The external dimensions of holster (305) may be identical to external dimensions and configurations as described for the above holster (205), and holsters (205, 305) may have the same grip area 190 as illustrated in FIG. 2. Top housing member (307) has an opening (311) therein exposing a portion of an intermediate driven gear (338) of cable driven cutter drive mechanism (310). A recess (304) is provided in top housing member (307) to receive central thumbwheel (60) of probe (105), and a thumbwheel drive slot (303) extends through recess (304) to expose a thumbwheel gear (350) of tissue holder rotational mechanism (340). As will be described in greater detail below, thumbwheel gear (350) is configured to rotatably engage with teeth (61) of central thumbwheel (60); and intermediate driven gear (338) is configured to rotatably engage with gear (85) extending from probe (105) when probe (105) is coupled with holster (305).

A. Exemplary Alternate Tissue Holder Rotation Mechanism

FIG. 15 shows probe (105) attached to holster (305) to show the exemplary tissue holder rotational mechanism (340). In this view, top housing member (307) of holster (305) is shown attached to probe (105), and bottom housing member (306) is shown as an outline to show elements within. For clarity in showing elements of the exemplary tissue holder rotational mechanism (340), elements of the exemplary cable driven cutter drive mechanism (310) are removed from this view with the exception of a drive cable (315) and certain rotatable elements associated therewith.

Central thumbwheel (60) of probe (105) is shown rotatably linked to manifold (144) located within tissue sample holder (140) via gear (170). This rotational linking is accomplished by engaging central thumbwheel (60) and manifold (144) with the exemplary tissue holder rotational mechanism (340) located within holster 305.

As shown in FIG. 15, thumbwheel gear (350) of tissue holder rotational mechanism (340) has plurality of teeth around a periphery thereof, and thumbwheel gear (350) extends through thumbwheel drive slot (303) in recess (304) of top housing member (307). When probe (105) is attached to holster (305) as shown, the plurality of teeth around a periphery of thumbwheel gear (350) are rotatably engaged with teeth (61) of thumbwheel (60). Rotation of thumbwheel (60) thus causes rotation of thumbwheel gear (350).

Tissue holder rotational mechanism (340) of the present example further comprises a rotary shaft (353) that extends proximally through a center of thumbwheel gear (350) and rotates with thumbwheel gear (350). A takeoff gear (355) is attached to the proximal end of shaft (353) and rotates with shaft (353). Shaft (353) and gears (350, 355) are supported by a distal bearing (382) mounted in a first rotary saddle (380); and by a proximal bearing (383) mounted in a secondary rotary saddle (381). Rotary saddles (380, 381) are configured to extend downward from the housing member (307). An intermediate gear (356) is engaged with the takeoff gear (355) and rotates therewith. Intermediate gear (356) is also rotatably engaged with a distal drive gear (357), such that rotation of the takeoff gear (355) rotates intermediate gear (356) and distal drive gear (357). A short drive shaft (359) extends longitudinally and proximally from distal drive gear (357) and is attached to a proximal takeoff gear (358). Proximal takeoff gear (358) is located below a proximal opening (279) at a proximal end of top housing member (307) and is accessible through opening (279). Thus, working through the gear train of the exemplary tissue holder rotational mechanism (340), rotation of thumbwheel gear (350) through slot (303) ultimately rotates proximal takeoff gear (358), which is exposed in proximal opening (279) at the proximal end of holster (350).

When probe (105) is attached to holster (305), thumbwheel (60) of probe (105) engages with thumbwheel gear (350) of holster (305), and the proximal takeoff gear (358) of holster (305) engages with holder gear (170) of probe (105). As shown in FIGS. 3-4 and 10, and as described above, holder gear 170 is directly coupled with manifold (144) within tissue sample holder (140). Thus, the attachment of probe (105) to holster (305) rotatingly couples thumbwheel (60) to manifold (144) via tissue holder rotational mechanism (340), and rotation of thumbwheel (60) thereby rotates manifold (144).

A gear drive ratio exists between the rotational input from thumbwheel (60) and the rotational output at manifold (144). Gear ratios within the holder rotational mechanism (340) directly affect the gear drive ratio. The gear drive ratio (input to output) can be configured by altering gear ratios of the holder rotational mechanism (340) such that a given degree of rotation of thumbwheel (60) produces a certain degree of rotation at manifold (144). Such a ratio may be 1:1, by way of example only. In alternate embodiments, the gear ratios can be altered so that a degree of rotation at thumbwheel (60) produces more than a degree of rotation at manifold (144), or a degree of rotation at thumbwheel (60) produces less than a degree of rotation at the manifold (144). Suitable ratios will be apparent to those of ordinary skill in the art in view of the teachings herein.

It should also be understood that rotation of manifold (144) may be provided in predefined increments, such as to provide some degree of self-alignment of each tissue sample chamber (166) with tissue sample passage (54). For instance, accurate indexing positions can be achieved using a spring loaded detent (not shown), using a self-aligning mechanism between a housing component of tissue sample holder (140) and light pipe (188) or some other component of probe (105); or using any other suitable components, features, configurations, or techniques. Tissue holder rotation mechanism (340) may also provide audible, visual, and/or tactile feedback to indicate successful alignment of a tissue sample chamber (166) with tissue sample passage (54). Still other suitable features, components, configurations, functionalities, and operational methods of holder rotation mechanism (340) will be apparent to those of ordinary skill in the art in view of the teachings herein.

B. Exemplary Cable Driven Cutter Drive Mechanism

In FIG. 16, all of the drive elements of a cable driven cutter drive mechanism (310) are shown in combination with tissue holder rotational mechanism (340). As will be described in detail below, portions of tissue holder rotational mechanism (340), such as a rotary shaft (353), are coaxially nested within a hollow idler shaft (332) of cable driven cutter drive mechanism (310). Shafts (353, 332) rotate independently from each other, and can rotate in the same time and/or opposite rotational directions.

Cutter drive mechanism (310) of the present example is substantially similar to cutter drive mechanism (210) of holster (205). For instance, cutter drive mechanism (310) comprises a drive cable (310) having an inner wire cable (317) and a sheath (319) and which enters through a bottom strain relief. These components respectively correlate with drive cable (215), wire cable (217), sheath (219), and strain relief (209) of holster (205). Cutter drive mechanism (310) further comprises a distal end connector (308); and a shock assembly (328) comprising a flex end coupling (322), a holster end coupling (324) fixedly attached to a cable drive gear (325), and an elastomeric shock absorber (323) that is captured between flex end coupling (322) and holster end coupling (324). These components respectively correlate with distal end connector (208, 308), shock assembly (228, 328), couplings (222, 224), cable drive gear (225), and shock absorber (223) of holster (205) as described above. Cutter drive mechanism (310) further comprises bearings (326, 327, 372, 373, 374 375 376, 377, 378), an idler driven gear (330), a hollow idler shaft (332), an idler drive gear (334), and an intermediate driven gear (338). These components respectively correlate with bearings (226, 227, 272, 273, 274 275 276, 277, 278), idler driven gear (230), hollow idler shaft (232), idler drive gear (234), and intermediate driven gear (238) of holster (205).

As shown, a portion of intermediate driven gear (338) extends through a slot (311) in top housing member (307) and is rotatably engaged with gear 85 of probe (105). Gear (85) is engaged with cutter rotation and translation mechanism (80) of probe (105) to simultaneously rotate and translate cutter (50) as described above. It will therefore be appreciated that rotation of cable (317) in the present example will cause simultaneous rotation and translation of cutter (50). Cutter drive mechanism (310) of probe (305) thus operates like cutter drive mechanism (210) of probe (205).

A hollow bore (not shown) extends longitudinally within the hollow idler shaft (332) to concentrically surround (without interferingly touching) rotary shaft (353) of tissue holder rotational mechanism (340). With this coaxially nested arrangement, either one of tissue holder rotational mechanism (340) or cutter drive mechanism (310) may rotate or otherwise be actuated independently without affecting the other.

Turning now to FIG. 17, drive elements of cutter drive mechanism (310) and tissue holder rotational mechanism (340) can be seen placed within bottom housing member (306). End connector (308) of cable sheath (319) is held within bottom housing member (306). Cable drive gear (325) and shock assembly (328) at a distal end of cable (317) are supported by bearings (326, 327) in bottom housing member (306). The assembly of thumbwheel gear (350), rotary shaft (353), and takeoff gear (355) are rotatably supported in bearings (382) in bottom housing member (306). A dual plate support structure comprising a bottom plate (390) and a top plate (391) mounts within bottom housing member (306), with proximal bearing (383) received within to support rotary shaft (353) and takeoff gear (355). Takeoff gear (355) is shown nested within a clearance slot (392) within top plate (391) just proximal to proximal bearing (383). Intermediate gear (356) that rotatably engages with takeoff gear (355) is supported below takeoff gear (355). Drive gear (357), short drive shaft (359), and proximal takeoff gear (358) thus rotatably mount between bottom plate (390) and top plate (391). Gears (357, 358) can be seen protruding from top plate (391). Middle plate (321) and an encoder assembly (340) are not shown in FIG. 17.

As will be appreciated, tissue holder rotational mechanism (340) may have a variety of alternative features, components, configurations, functionalities, and methods of operations. Furthermore, tissue holder rotational mechanism (340) may have any other suitable relationships with cutter drive mechanism (210). Suitable alternatives will be apparent to those of ordinary skill in the art in view of the teachings herein.

C. Exemplary Idler Shaft Encoder for Cutting Mechanism

As shown in FIG. 16, an encoder assembly (340) mounts to a proximal end of the idler shaft (332) and is operably connected to motor (530) via wiring (not shown) extending between holster (305) and vacuum control module (500). Encoder assembly (340) may be configured and used in the same way as encoder assembly (240) of holster (205) described above. Alternatively, encoder assembly (340) may be configured and/or used in any other suitable fashion, if not omitted altogether.

D. Exemplary Alternative Tissue Sample Holder

Figure 18:
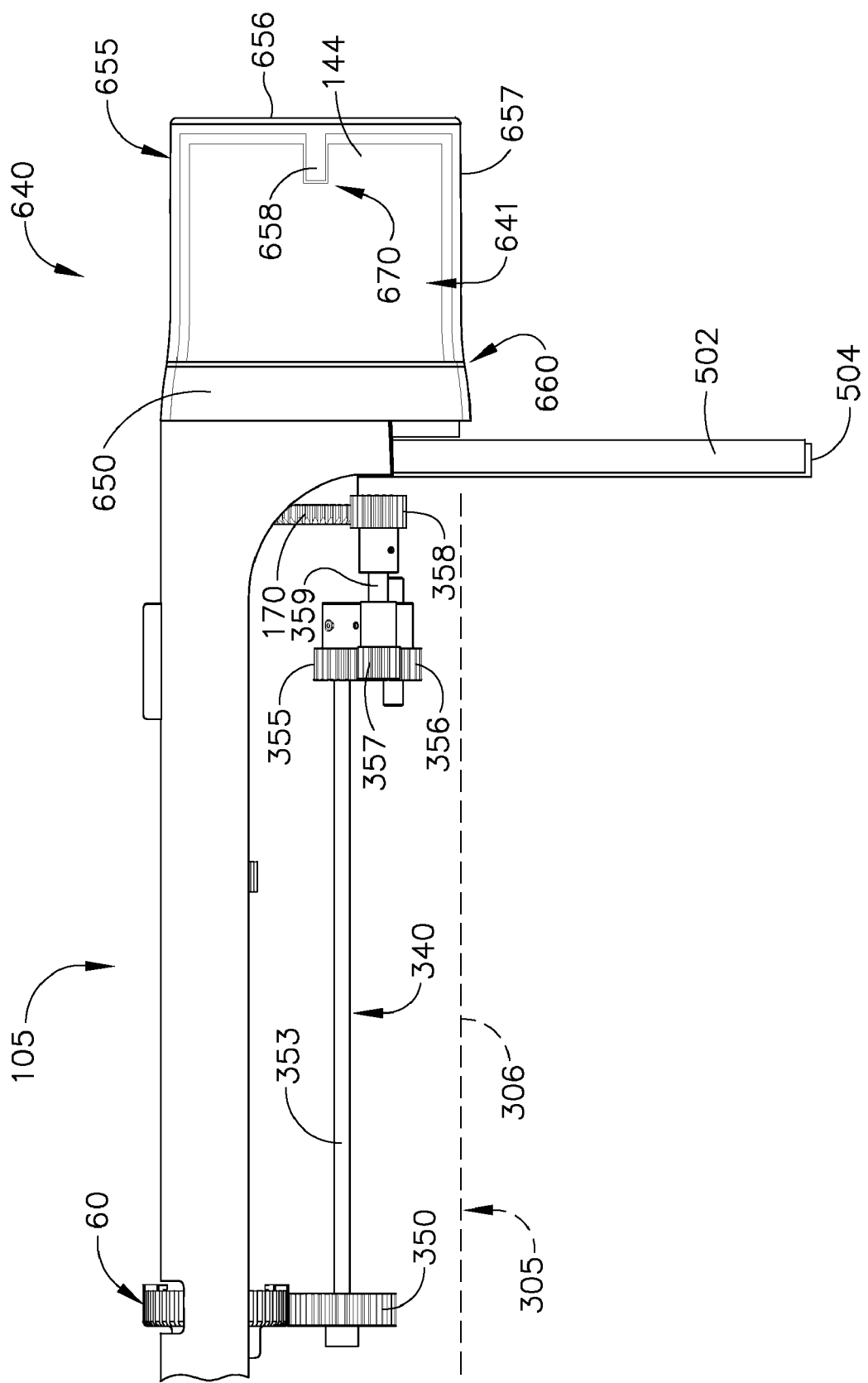
FIG. 18 is a partial side view of an exemplary alternate tissue sample holder coupled with the tissue sample holder drive system of FIG. 15.

A probe (105) that is coupled with holster (305) may have tissue sample holder (140) described above. Alternatively, as shown in FIG. 18, cup (141) of tissue sample holder (140) may be substituted with a split removable cup assembly (641), which may be coupled with probe (105) and holster (305), to provide an alternative tissue sample holder (640). Split removable cup assembly (641) of this example comprises a rotating cup (655) that attaches to probe (105) over manifold (144). Cup (655) is manually operable to rotate manifold (144) in this example. A locking ring (650) releasably attaches to probe (105), and rotatingly secures cup (655) to probe (105). In particular, locking ring (650) secures cup (655) to probe (105) while permitting cup (655) to rotate relative to locking ring (650) and probe (105). For instance, cup (655) and locking ring (650) may include complementary annular flanges (not shown) or other features to restrict longitudinal motion of cup (655) relative to locking ring (650). Locking ring (105) does not move relative to probe (105) while cup (655) rotates in this example.

Rotating cup (655) has a proximal end wall (656) and a sidewall (657). Sidewall (657) and/or proximal end wall (656) may provide a grasping portion for the operator to grasp. Such a grasping portion may include texture, bumps, ridges, or any other features to enhance grasping of the grasping portion and rotation of rotating cup (655). Alternatively, a feature such as an integral knob or other protrusion may extend proximally from proximal end wall (656). A vacuum or fluid seal (660) is placed between locking ring (650) and rotating cup (655), and maintains fluid or vacuum integrity therebetween, both when cup (655) is rotated relative to ring (650) and when cup (655) is stationary relative to ring (650). Locking ring (650) may be configured with the previously described bayonet coupling (134) as shown in FIG. 3 for use as a releasable attachment mechanism to probe (105). Alternatively, any other suitable structures or configurations may be used.

Split removable cup assembly (641) is further configured with one or more inward extending drive members (658) to drivably engage with rotatable manifold (144), and when engaged, to rotate therewith. Drive member (658) may comprise a keyed pin, a "D" shaft, a hex shaft, or any other suitable structure, and may extend inward from an inside surface of proximal end wall (656) to drivingly engage with a drive hole (670) within rotatable manifold (144). When split removable cup assembly (641) is attached to bring drive member (658) into engagement with drive hole (670), and when manifold (144) rotates, rotating cup (655) rotates therewith. Conversely, as described in detail below, rotation of rotating cup (655) may rotate manifold (144).

As described above, gear (170) is secured to manifold (144), such that gear (170) and manifold (144) rotate unitarily. As also described above, and with reference to FIG. 15, gear (170) is coupled with thumbwheel (60) via gears (358, 357, 356, 355, 350) and shafts (359, 353), such that gear (170) and thumbwheel rotate concomitantly. As also described above, and with reference to FIGS. 5-6, thumbwheel (60) is secured to cannula (12), such that rotation of thumbwheel (60) rotates cannula (12) (e.g., to angularly reorient aperture (16)). Accordingly, those of ordinary skill in the art will appreciate that an operator may manually rotate cup (655) to rotate cannula (12) (e.g., to angularly reorient aperture (16)).

To assemble split removable cup assembly (641), cup (655) may be placed over rotatable manifold (144) to engage drive member (658) of cup (655) with drive hole (670) in rotatable manifold (144). Once drive member (658) is engaged with drive hole (670), locking ring (650) may be secured to probe (105) by rotating locking ring (650) to engage bayonet coupling (134). In this configuration, rotation of thumbwheel (60) on probe (105) will rotate needle portion (10), manifold (144), and rotating cup (655). If desired, the operator may rotate needle portion (10) by manually rotating the rotating cup (655).

Of course, a variety of other components, features, structures, and configurations may be used in addition to or in lieu of split removable cup assembly (641). By way of example only, manifold (144) may be fitted with an integral and proximally extending knob (not shown) or other feature that protrudes through cup (141). Cup (141) may accommodate such a knob or other feature with a seal, such that the knob or other feature may rotate relative to cup (141) without causing loss of vacuum or fluids. In such versions, it will be understood that the operator may rotate needle portion (10) by manually rotating the knob or other feature that extends proximally from manifold (144) through cup (141). In some other variations, tissue sample holder (140) is configured in accordance with any of the teachings of U.S. Non-Provisional patent application Ser. No. [FBT DOCKET NO. 0021680.END6471USNP], entitled "BIOPSY DEVICE WITH DISCRETE TISSUE CHAMBERS," filed on even date herewith, the disclosure of which is incorporated by reference herein. Still other suitable components, features, structures, and configurations that may be used to permit rotation of needle portion from a tissue sample holder (140) will be apparent to those of ordinary skill in the art in view of the teachings herein.

E. Exemplary Method of Use of the Second Exemplary Biopsy Device

In a merely exemplary use of biopsy device (101), biopsy device (101) is assembled by operably coupling probe (105) with holster (305) and then operably coupling the assembled biopsy device (101) with vacuum control module (500). With probe (105) attached to holster (305), thumbwheel (60) is rotatingly engaged with the tissue holder rotational mechanism (340) in holster (305), and is therefore rotatingly engaged with rotatable manifold (144) within tissue sample holder (140). Furthermore, with probe (105) attached to holster (305), gears (338, 84) are coupled such that cutter drive mechanism (310) within holster (350) is operably engaged with cutter (50) within the probe (105). With the cable driven cutter drive mechanism (310) operably engaged with cutter (50), homing routines may be performed, if required or desired, to identify a "home" position of cutter (50) within probe (105).

An operator then places biopsy device (101) into a grasping hand (1000) and/or couples biopsy device (101) with a fixture or targeting set. Needle portion (10) is then inserted into a patient's breast or elsewhere. The operator then rotates thumbwheel (60) with a thumb or other finger to achieve a desired angular orientation of aperture (16). Such rotation will also cause rotation of manifold (144). The operator then actuates cutter (50) to acquire a tissue sample, which is communicated to a tissue sample chamber (166) in tissue sample holder (140) via cutter lumen (52) and tissue sample passage (54). With needle portion (10) still inserted in the patient, the operator rotates thumbwheel (60) to simultaneously reorient aperture (16) and index another tissue sample chamber (166) to tissue sample passage (54). The operator then actuates cutter (50) to acquire another tissue sample. This process may be repeated until a desired number of tissue samples are obtained at a desired number of angular orientations about the axis defined by needle portion (10). Of course, biopsy device (101) may alternatively be used in any other desired fashion.

III. Third Exemplary Holster

Figure 19:
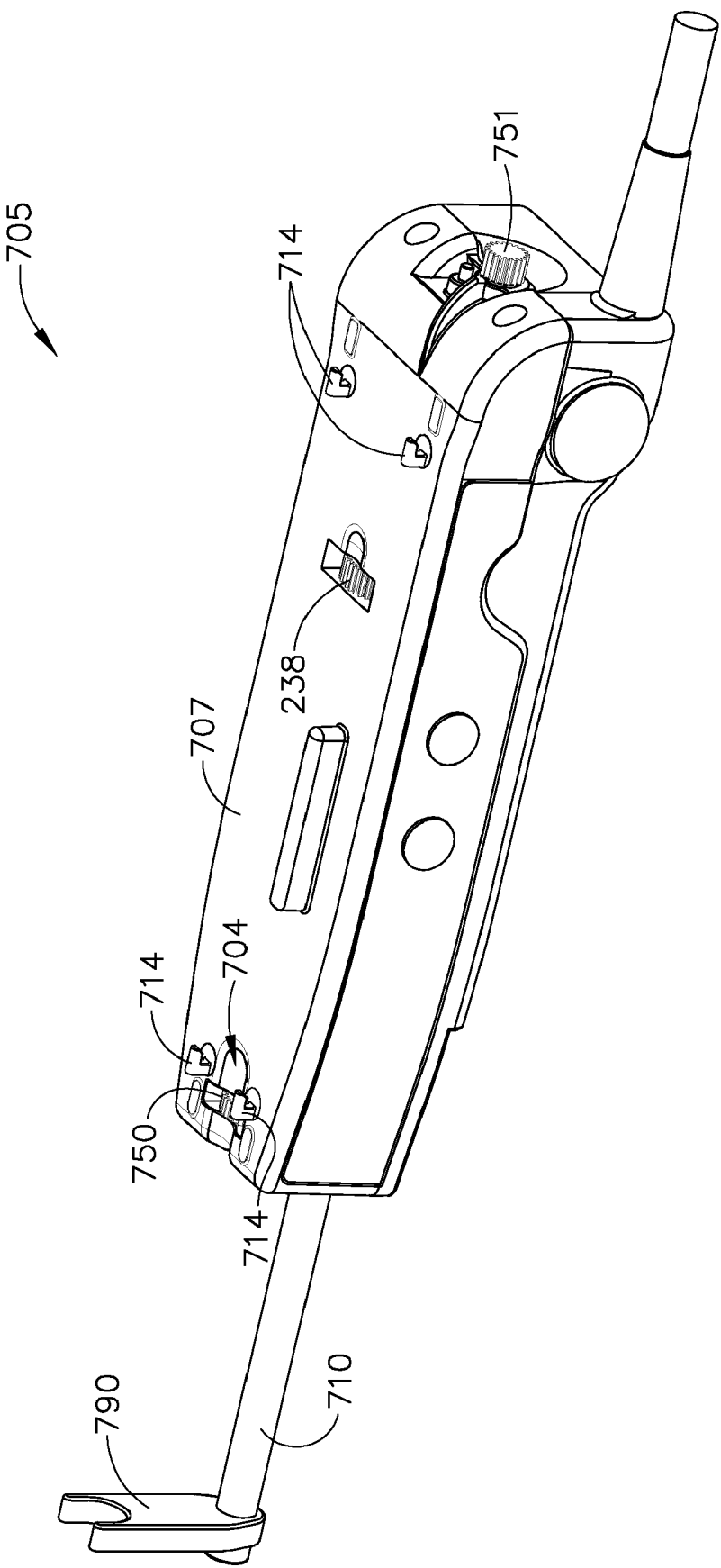
FIG. 19 is a perspective view of another exemplary holster.
Figure 20:
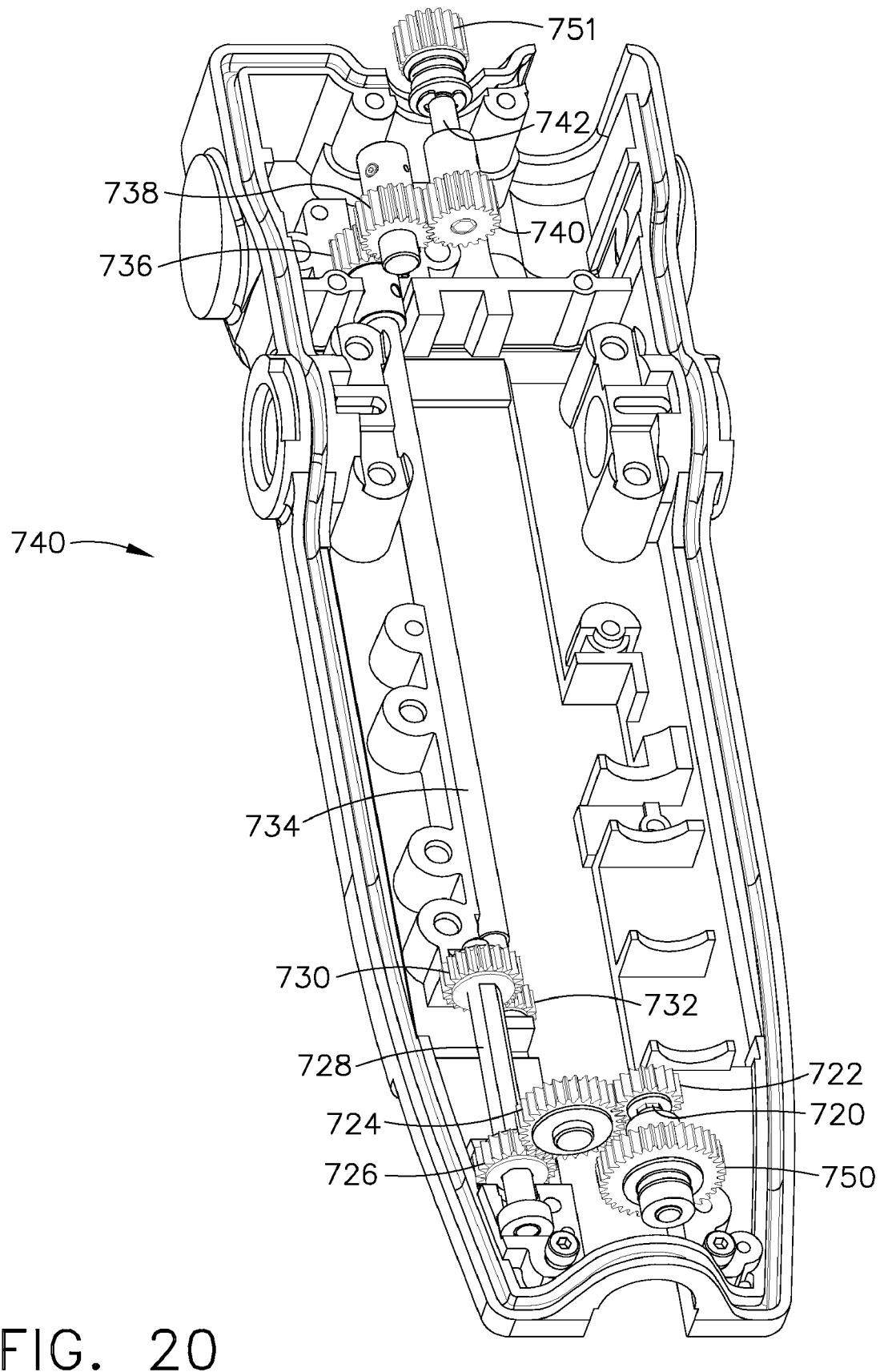
FIG. 20 is a perspective view of the holster of FIG. 19, with components removed to show an exemplary linking mechanism.

FIGS. 19-20 show another exemplary holster (705). Holster (705) of this example is configured for use in a stereotactic setting. By way of example only, holster (705) may be coupled with probe (105), with a probe as described in U.S. Pub. No. 2008/0195066, entitled "Revolving Tissue Sample Holder For Biopsy Device," published Aug. 14, 2008, the disclosure of which is incorporated by reference herein, or with any other suitable probe. Holster (705) comprises a top housing member (707), a bottom housing member (708), and a needle firing fork (790). Needle firing form (790) is positioned on the distal end of a needle firing shaft (710), which extends distally from holster (705). Holster (705) further comprises hook members (714), which extend from top housing member (707), and which may removably secure probe (105) to holster (705).

Top housing member (707) further comprises a recess (704) exposing a thumbwheel gear (750). Thumbwheel gear (750) is configured to mesh with thumbwheel (60) when probe (105) is coupled with holster (705). In particular, thumbwheel gear (750) is operable to rotate in response to manual rotation of thumbwheel (60) when probe (105) is coupled with holster (705). A tissue holder drive gear (751) extends from a proximal end of holster (705). Gear (751) is configured to mesh with gear (170) of tissue sample holder (140). In particular, gear (751) is operable to rotate manifold (144) of tissue sample holder (140) when probe (105) is coupled with holster (705), in the manner described above.

A linking mechanism (740) links thumbwheel gear (750) with gear (751). In particular, linking mechanism (740) is configured to cause gear (751) to rotate in response to rotation of thumbwheel gear (750). Linking mechanism (740) of this example comprises a shaft (720) extending proximally from thumbwheel gear (750). Another gear (722) is fixed to shaft (720). Gear (722) thus rotates with shaft (720) and with gear (750). Gear (722) also meshes with gear (724), which also meshes with gear (726). Gear (726) thus rotates with gears (722, 724). A shaft (728) extends proximally from gear (726). Another gear (730) is fixed to shaft (728). Gear (730) thus rotates with shaft (728) and with gear (726). Gear (730) also meshes with gear (732). A shaft (734) extends proximally from gear (732). Another gear (736) is fixed to shaft (734). Gear (736) thus rotates with shaft (734) and with gears (730, 732). Gear (736) also meshes with gear (738), which also meshes with gear (740). Gear (740) thus rotates with gears (736, 738). A shaft (742) connects gear (740) with gear (751). Accordingly, thumbwheel gear (750) is coupled with gear (751) via gears (722, 724, 726, 730, 732, 736, 738, 740) and shafts (720, 728, 734, 742). Linking mechanism (740) is thus similar to tissue holder rotational mechanism (340) of holster (305). Of course, other suitable components, features, configurations, and methods of operation for a linking mechanism (740) such as the one in holster (705) will be apparent to those of ordinary skill in the art in view of the teachings herein.

It should also be understood that a probe (105) with tissue sample holder (640) may be coupled with holster (705). In such a version, rotation of cup (655) may cause rotation of needle portion (10) as described above, via linking mechanism (740) or otherwise.

A cutter drive mechanism (not shown) is also provided within holster (705). In particular, the cutter drive mechanism is operable to rotate gear (238), which is exposed through top housing member (707). Gear (238) is configured to mesh with gear (85) when probe (105) is coupled with holster (705). Accordingly, rotation of gear (238) causes concomitant rotation and translation of cutter (50) when probe (105) is coupled with holster (705). Exemplary components, features, configurations, and methods of operation for a cutter drive mechanism such as the one in holster (705) are described in U.S. Pub. No. 2008/0195066, entitled "Revolving Tissue Sample Holder For Biopsy Device," published Aug. 14, 2008, the disclosure of which is incorporated by reference herein. Other suitable components, features, configurations, and methods of operation for a cutter drive mechanism such as the one in holster (705) will be apparent to those of ordinary skill in the art in view of the teachings herein.

A needle firing mechanism (not shown) is also provided within holster (705). In particular, the needle firing mechanism is operable to cause shaft (710) and fork (790) to translate longitudinally relative to holster (705). Fork (790) is configured to engage needle portion (10), such that needle portion (10) will translate longitudinally with shaft (710) and fork (790) when probe (105) is coupled with holster (705). Suitable modifications to probe (105) to permit needle portion (10) to translate longitudinally relative to other components of probe (105) will be apparent to those of ordinary skill in the art in view of the teachings herein. Alternatively, any probe disclosed in U.S. Pub. No. 2008/0195066, entitled "Revolving Tissue Sample Holder For Biopsy Device," published Aug. 14, 2008, the disclosure of which is incorporated by reference herein, may have its needle portion coupled with and translated by fork (790). In either case, such firing of needle portion (10) may be desired to forcibly urge needle portion (10) into breast tissue or other tissue. Exemplary components, features, configurations, and methods of operation for a needle firing mechanism such as the one in holster (705) are described in U.S. Pub. No. 2008/0195066, entitled "Revolving Tissue Sample Holder For Biopsy Device," published Aug. 14, 2008, the disclosure of which is incorporated by reference herein. Other suitable components, features, configurations, and methods of operation for a needle firing mechanism such as the one in holster (705) will be apparent to those of ordinary skill in the art in view of the teachings herein.

IV. Fourth Exemplary Holster

Figure 21:
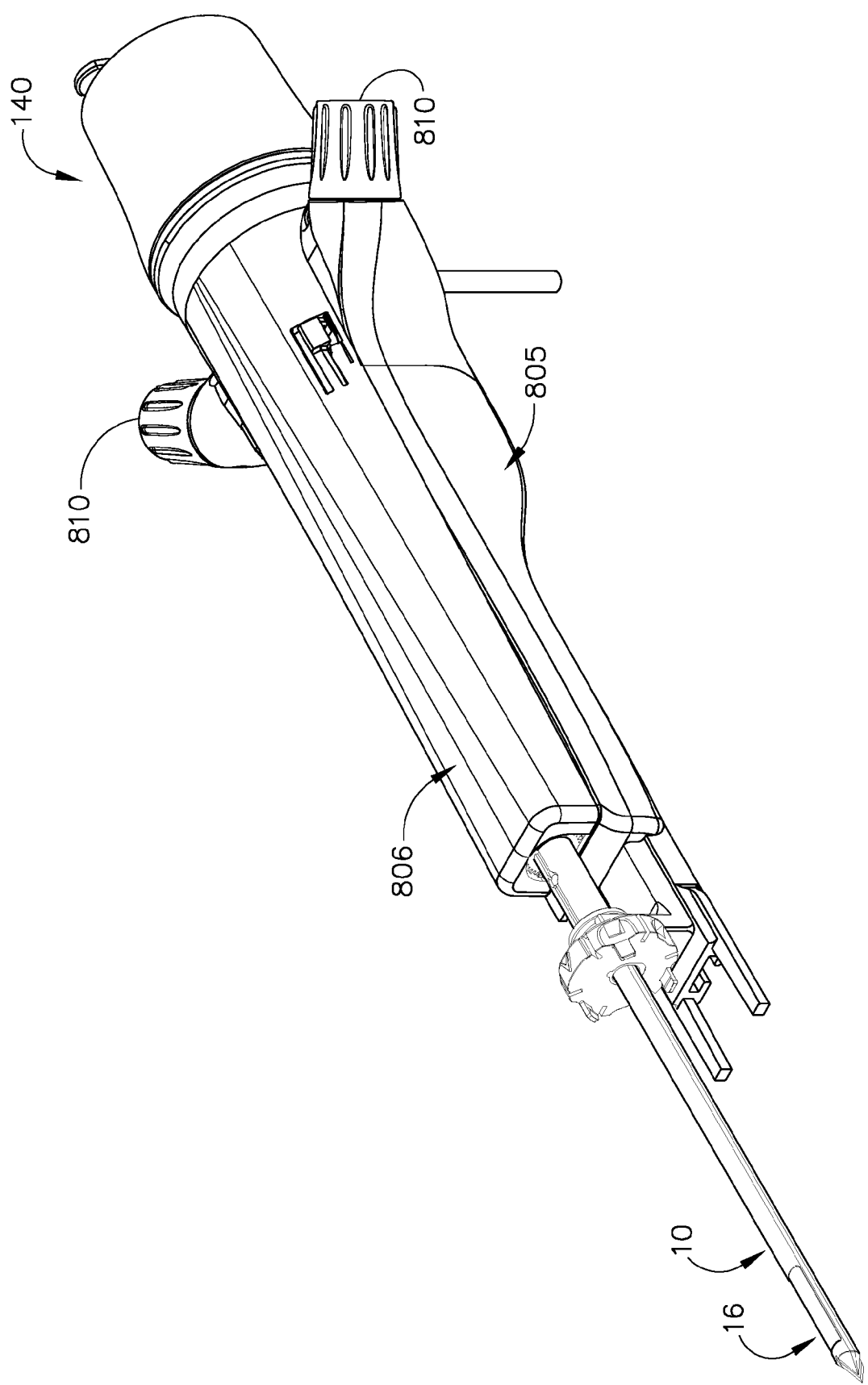
FIG. 21 is a perspective view of another exemplary probe coupled with another exemplary holster, with inclined thumbwheels.
Figure 22:
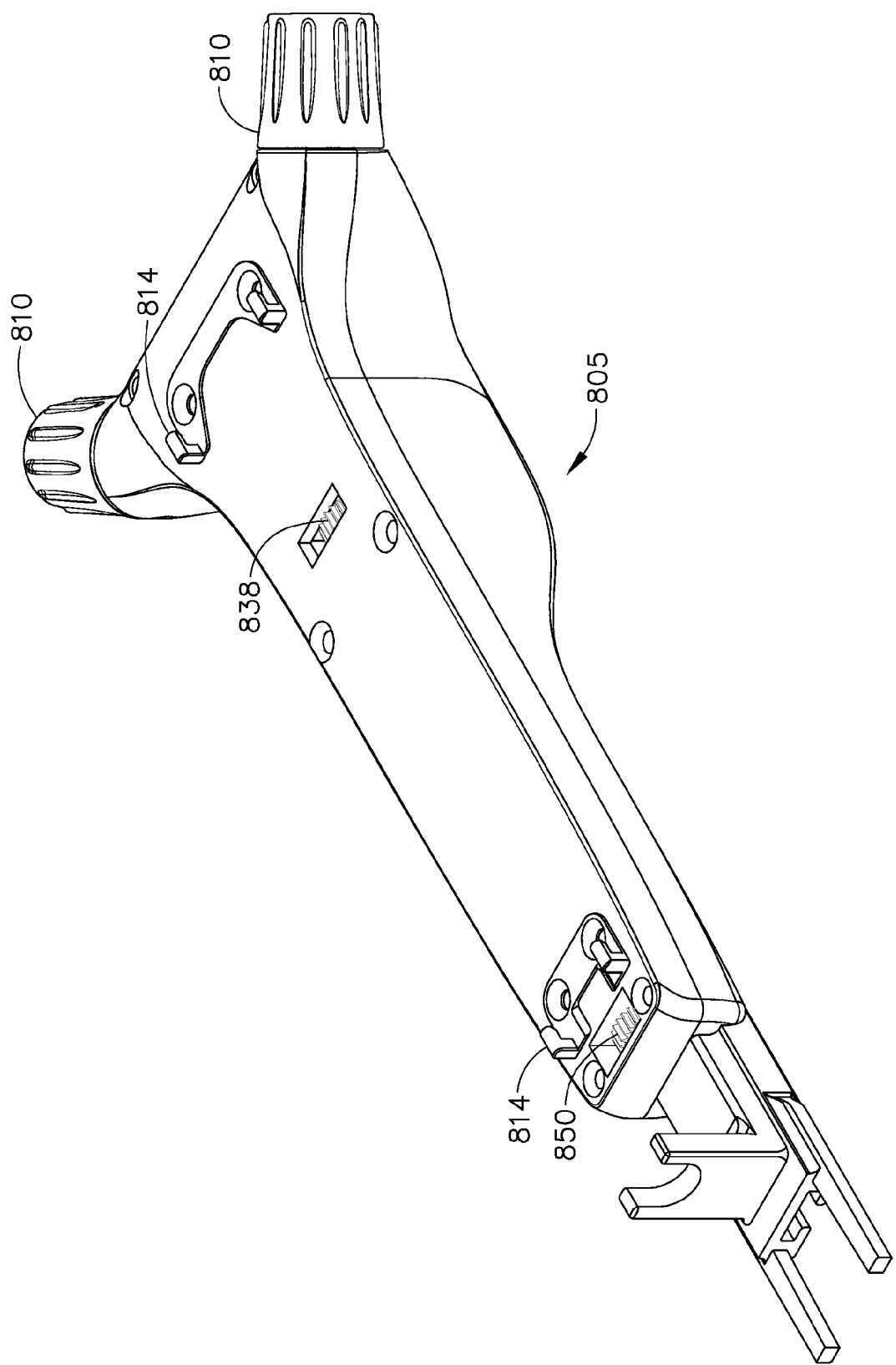
FIG. 22 is a perspective view the holster of FIG. 21.

FIGS. 21-22 show another exemplary holster (805), coupled with a probe (806). Probe (806) of this example is constructed in accordance with the teachings of U.S. Pub. No. 2008/0195066, entitled "Revolving Tissue Sample Holder For Biopsy Device," published Aug. 14, 2008, the disclosure of which is incorporated by reference herein. Alternatively, holster (805) may be configured to couple with probe (105) or with any other suitable probe. Probe (806) of the present example comprises a needle portion (10) that has a tissue receiving aperture (16), like probe (105) described above. Probe (806) of the present example also has a rotatable tissue sample holder (140), like probe (105) described above.

Holster (805) of the present example comprises hook members (814) that are configured to removably secure probe (806) to holster (805). Holster (805) further comprises gears (850, 838) and inclined thumbwheels (810). Gear (850) is configured to mesh with a needle gear (not shown) of probe (806). Such a needle gear is secured to needle portion (10) of probe (806) such that needle portion (10) rotates with the needle gear. Examples of such a needle gear are disclosed in U.S. Pub. No. 2008/0195066, entitled "Revolving Tissue Sample Holder For Biopsy Device," published Aug. 14, 2008, the disclosure of which is incorporated by reference herein, though any other types of needle gears may be used.

Gear (838) is configured to mesh with a cutter gear (not shown) of probe (806). In particular, probe (806) comprises a cutter rotation and translation mechanism (80) like probe (105), which presents the cutter gear through the bottom of probe. The cutter rotation and translation mechanism is operable to rotate and translate a cutter (50) within needle portion (10). Gear (838) is thus operable to actuate a cutter (50) within needle portion (10) of probe (806). A motor (not shown) or other mechanism may be provided within holster (805) to drive gear (838). Alternatively, gear (838) may be driven by a cable (217), such as in a manner similar to cable (217) driven techniques described herein.

The proximal end of holster (805) may also present a tissue sample holder rotation gear (not shown), which may be configured to mesh with a gear (170) of tissue sample holder (140) when probe (806) is coupled with holster (805).

Thumbwheels (810) are coupled with gear (850) in this example, such that thumbwheels (810) may be used to rotate needle portion (10). In particular, holster (805) includes a linking mechanism (not shown) that links thumbwheels (810) with gear (850), such that rotation of either thumbwheel (810) causes concomitant rotation of needle portion (10). Suitable components, features, and configurations of such a linking mechanism will be apparent to those of ordinary skill in the art in view of the teachings herein. By way of example only, such a linking mechanism may include a plurality of gears (e.g., one or more bevel gears), shafts, and/or universal joints. Such a linking mechanism may also be constructed similar to other such linking mechanisms described herein.

It should also be understood that thumbwheels (810) may be coupled with a tissue sample holder rotation gear of holster (805). In particular, thumbwheels (810) may be linked with a tissue sample holder rotation gear such that rotation of either thumbwheel (810) causes concomitant rotation of manifold (144) within tissue sample holder (140). Such coupling may be provided by the same linking mechanism noted above, which couples thumbwheels (810) with gear (850), or by some other linking mechanism. Again, suitable components, features, and configurations for coupling thumbwheels (810) with a tissue sample holder rotation gear will be apparent to those of ordinary skill in the art in view of the teachings herein.

In some versions of holster (805), one thumbwheel (810) is linked with gear (850), while the other thumbwheel (810) is linked with a tissue sample holder rotation gear. Holster (805) may thus have two or more linking mechanisms, which may be either mechanically independent of each other or somehow interdependent.

V. Fifth Exemplary Holster

Figure 23:
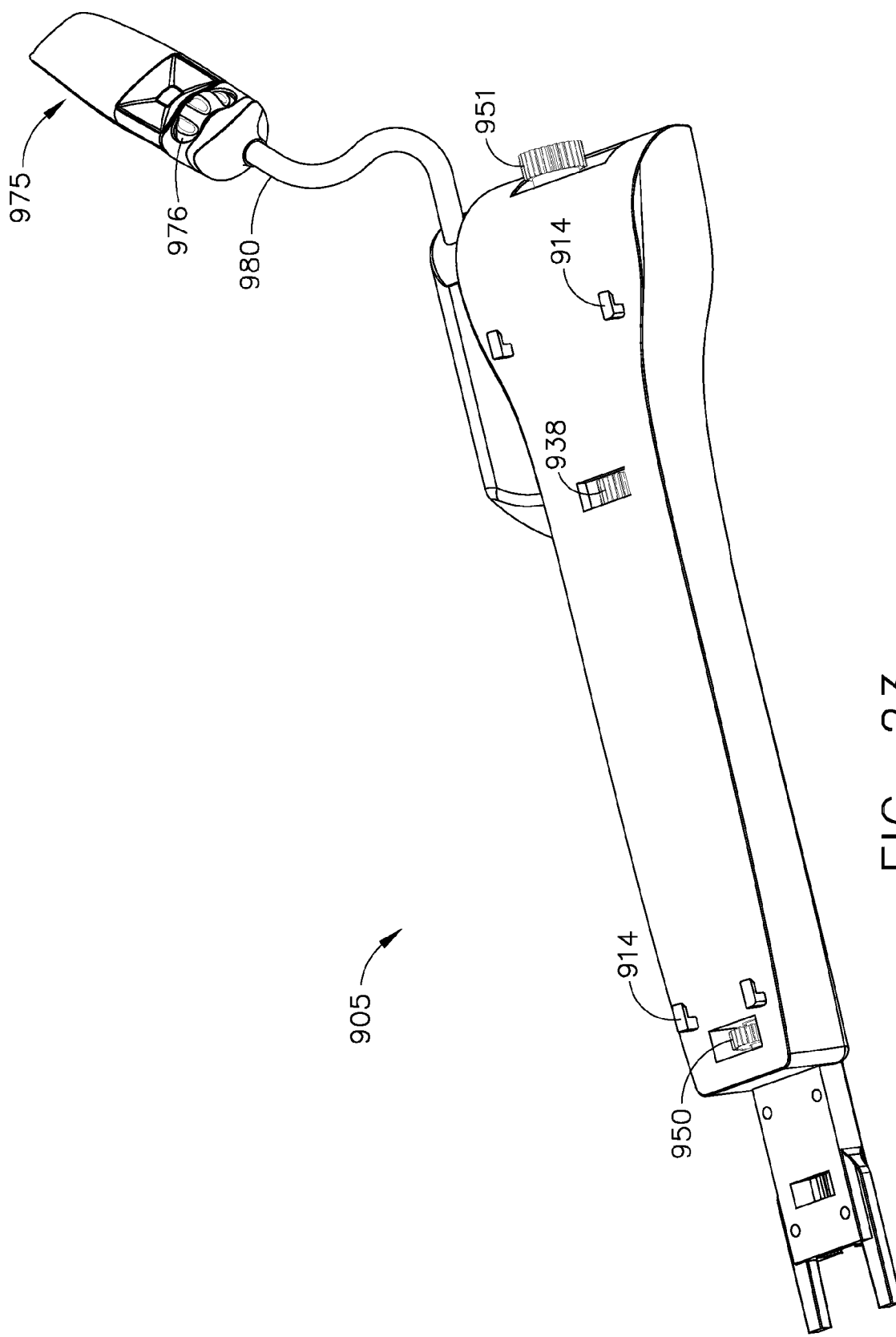
FIG. 23 is a perspective view of another exemplary holster, with a remote thumbwheel.

FIG. 23 shows yet another exemplary holster (905). Holster (905) of this example may be coupled with probe (806), probe (105), or any other suitable probe. Holster (905) comprises hook members (914) that are configured to removably secure probe (806, 105) with holster (905). Holster (905) further comprises gears (950, 938, 951), portions of which are exposed by holster (905). Gear (950) is configured to mesh with a needle gear (not shown) of probe (806). Such a needle gear is secured to needle portion (10) of probe (806) such that needle portion (10) rotates with the needle gear. Examples of such a needle gear are disclosed in U.S. Pub. No. 2008/0195066, entitled "Revolving Tissue Sample Holder For Biopsy Device," published Aug. 14, 2008, the disclosure of which is incorporated by reference herein, though any other types of needle gears may be used.

Gear (938) is configured to mesh with a cutter gear (not shown) of probe (806). In particular, probe (806) comprises a cutter rotation and translation mechanism (80) like probe (105), which presents the cutter gear through the bottom of probe. The cutter rotation and translation mechanism is operable to rotate and translate a cutter (50) within needle portion (10). Gear (938) is thus operable to actuate a cutter (50) within needle portion (10) of probe (806). A motor (not shown) or other mechanism may be provided within holster (905) to drive gear (938). Alternatively, gear (938) may be driven by a cable (217), such as in a manner similar to cable (217) driven techniques described herein.

The proximal end of holster (905) also presents tissue sample holder rotation gear (951), which is configured to mesh with a gear (170) of tissue sample holder (140) when probe (806) is coupled with holster (905).

A remote control (975) is coupled with holster (905) in this example via a flexible drive cable assembly (980). Drive cable assembly (980) comprises a drive cable (not shown), much like drive cable (217) described above, with a surrounding sheath. In particular, the drive cable of drive cable assembly (980) is operable to communicate rotary motion from remote control (975) to holster (905). Drive cable assembly (980) is also flexible, such that the drive cable of drive cable assembly (980) may still communicate rotary motion to holster (905) even while being flexed, without binding. Remote control (975) comprises a manually rotatable thumbwheel (976) that is coupled with the drive cable of drive cable assembly (980). In particular, manual rotation of thumbwheel (976) rotates the drive cable of drive cable assembly (980).

Thumbwheel (976) and the drive cable of drive cable assembly (980) are coupled with gear (950) in this example, such that thumbwheel (976) may be used to rotate needle portion (10) of a probe (806, 105) that is coupled with holster (905). In particular, holster (905) includes a linking mechanism (not shown) that links thumbwheel (976) and the drive cable of drive cable assembly (980) with gear (950), such that rotation of thumbwheel (976) causes concomitant rotation of needle portion (10). Suitable components, features, and configurations of such a linking mechanism will be apparent to those of ordinary skill in the art in view of the teachings herein. By way of example only, such a linking mechanism may include a plurality of gears (e.g., one or more bevel gears), shafts, and/or universal joints. Such a linking mechanism may also be constructed similar to other such linking mechanisms described herein.

It should also be understood that thumbwheel (976) and the drive cable of drive cable assembly (980) may be coupled with tissue sample holder rotation gear (951). In particular, thumbwheel (976) and the drive cable of drive cable assembly (980) may be linked with tissue sample holder rotation gear (951) such that rotation of thumbwheel (976) causes concomitant rotation of manifold (144) within tissue sample holder (140) of a probe (806, 105) that is mounted to holster (905). Such coupling may be provided by the same linking mechanism noted above, which couples thumbwheel (976) with gear (950), or by some other linking mechanism. Again, suitable components, features, and configurations for coupling thumbwheel (976) with a tissue sample holder rotation gear will be apparent to those of ordinary skill in the art in view of the teachings herein.

It should also be understood that drive cable assembly (980) may be of any suitable length. For instance, drive cable assembly (980) may be less than one foot long, four feet long, ten feet long, or any other suitable length.

VI. Exemplary Vacuum Control Module and Canister

As shown in FIG. 1, an exemplary vacuum canister (600) is configured to be coupled vacuum control module (500). Vacuum control module (500) is operable to induce a vacuum through vacuum canister (600), and such a vacuum may be communicated to probe (105) via tubes (502, 504). For instance, vacuum control module (500) may communicate a vacuum through tube (502), which may then communicate the vacuum through tissue sample holder (140) to cutter lumen (52) as described above. Vacuum control module (500) may also communicate a vacuum through tube (504) to manifold (70), which may then communicate the vacuum to vacuum lumen (40) as described above.

Furthermore, vacuum canister (600) is operable to collect fluids that are communicated from biopsy probe (105) during use of biopsy probe (105). Vacuum canister (600) may thus be regarded as providing a fluid interface between biopsy probe (105) and vacuum control module (500). Any suitable vacuum control module and vacuum canister may be used such as those described in U.S. Pub. No. 2008/0195066, entitled "Revolving Tissue Sample Holder For Biopsy Device," published Aug. 14, 2008, the disclosure of which is incorporated by reference herein. Further, any other suitable component, system, technique, or device may be used with the suitable control module or vacuum canister.

As noted above, vacuum control module (500) of the present example also includes a motor (503) that is operable to rotate cable (217), such as to actuate cutter (50) as described above. By way of example only, motor (503) may be associated with vacuum control module (400) as taught in U.S. Non-Provisional patent application Ser. No. [FBT DOCKET NO. 0021680.END6466USNP], entitled "CONTROL MODULE INTERFACE," filed on even date herewith, the disclosure of which is incorporated by reference herein. Of course, the features and functionality of vacuum control module (500) and vacuum canister (600) as described herein are mere examples.

VIII. Exemplary Modes of Operation

It will be appreciated in view of the disclosure herein that there are a variety of methods by which biopsy system (2) may be operated. For instance, regardless of the structures or techniques that are used to selectively control communication of fluid (e.g., saline, vacuum, venting, etc.), through conduits (501) or otherwise within biopsy system (2), there are a variety of timing algorithms that may be used. Such timing algorithms may vary based on an operational mode selected by a user. Furthermore, there may be overlap among operational modes (e.g., biopsy system (2) may be in more than one operational mode at a given moment, etc.). In addition to fluid communication timing algorithms being varied based on a selected mode of operation, other operational aspects of biopsy system (2) may vary based on a selected operational mode. Several merely exemplary operational modes exist, while others will be apparent to those of ordinary skill in the art in view of the teachings herein. Any suitable operational mode may be used include for example any suitable mode disclosed in U.S. Pub. No. 2008/0195066, entitled "Revolving Tissue Sample Holder For Biopsy Device," published Aug. 14, 2008, the disclosure of which is incorporated by reference herein.

One exemplary operation of biopsy system (2) will now be explained where needle portion (10) has been inserted into the breast of a patient. With needle portion (10) inserted, lateral and axial vacuum are applied. In particular, a vacuum is communicated through tubes (502, 504). Given the fluid connection of tube (504) with vacuum lumen (40) of outer cannula (12), communication of a vacuum through tube (504) will draw a lateral vacuum relative to cannula lumen (20). Communication of a vacuum through tube (502) will draw an axial vacuum through cutter lumen (52), given the fluid connection of tube (502) to cutter lumen (52) via tissue sample holder (140) and passage (54) in this example.

With the axial and lateral vacuum applied as described above, cutter (50) is retracted axially. The axial retraction of cutter (50) will serve to "open" aperture (16), which results in tissue prolapsing into aperture (16) under the influence of the above-described vacuums. Cutter (50) may dwell in a retracted position for a certain period of time to ensure sufficient prolapse of tissue.

Next, cutter (50) is advanced distally to sever tissue that is prolapsed through aperture (16). As the distal end of cutter (50) passes the distal edge of aperture (16), such that cutter (50) "closes" aperture (16), the prolapsed tissue should be severed and at least initially contained within cutter lumen (52). Transverse openings (32) should be configured such that at least one or more of openings (32) are not covered by cutter (50) when cutter (50) has reached a position to "close" aperture (16). With aperture (16) closed and a vent being provided by transverse openings (32) through tube (504), an axial vacuum being communicated through cutter lumen (52) by tube (502) should draw the severed tissue sample proximally through cutter lumen (52) and into a tissue sample chamber (166) of tissue sample holder (140). Cutter (50) may be reciprocated one or more times through a slight range of motion at a distal position to sever any remaining portions that may have not been completely severed in the first pass of cutter (50).

Before tissue sample is communicated proximally through cutter lumen (52), with aperture (16) being closed by cutter (50), vacuum lumen (40) being vented by tube (504), and an axial vacuum being provided by tube (502) via cutter lumen (52), cutter (50) is retracted slightly to expose a portion of aperture (16) for a short period of time. During this time, saline may be provided at atmospheric pressure to vacuum lumen (40) by tube (504). Further retraction of cutter (50) exposes more transverse openings (32), thereby increasing fluid communication between vacuum lumen (40) and cannula lumen (20). Retraction of cutter (50) also exposes the pressure of the tissue cavity (from which tissue sample was obtained) to the distal surface of tissue sample. As a result of the slight retraction of cutter (50) in this particular example, the likelihood of atmospheric pressure being applied to the distal face of tissue sample may be increased to help ensure that severed tissue sample does not remain in needle portion (10) (a.k.a. a "dry tap"). Cutter (50) is then fully advanced distally, closing both aperture (16) and all transverse openings of outer cannula (12). Such "closure" of transverse openings may ensure that if medication is applied at this time (between samples) to reduce pain, it will reach the breast cavity through external openings in outer cannula (12) instead of being aspirated through transverse openings and through cutter lumen (52) and tissue sample holder (140).

With the cutter (50) being completely advanced (e.g., such that all transverse openings and aperture (16) are closed), and severed tissue sample being communicated proximally through cutter lumen (52) and into a tissue sample chamber (166) by an axial vacuum drawn by tube (502), biopsy device (100) will be in a ready state. In this ready state, vacuum lumen (40) is vented to atmosphere, and axial vacuum tube (502) is sealed (a.k.a. "dead-headed").

Other suitable components of, features of, configurations of, and methods of operating biopsy system (2) are disclosed in U.S. Pub. No. 2008/0195066, entitled "Revolving Tissue Sample Holder For Biopsy Device," published Aug. 14, 2008, the disclosure of which is incorporated by reference herein. Still other suitable components of, features of, configurations of, and methods of operating biopsy system (2) will be apparent to those of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy device for acquiring tissue samples from a patient, the biopsy device comprising:
   a probe, comprising:
      a needle portion having a tissue receiving aperture, wherein the needle portion defines a longitudinal axis,
      a body portion having a distal end and a proximal end, wherein the needle portion extends distally from the distal end of the body portion, a rotatable thumbwheel coupled with the needle portion, wherein the rotatable thumbwheel is fixedly secured relative to the needle portion such that the thumbwheel is operable to rotate the needle portion about the longitudinal axis, a cutter longitudinally movable within the needle portion, wherein the cutter is configured to cut tissue protruding into the aperture, wherein the cutter defines a cutter lumen, and a rotatable tissue sample holder configured to receive tissue samples severed by the cutter and communicated through the cutter lumen; and a holster removably coupled with the probe, the holster comprising a linking mechanism, wherein the thumbwheel is rotatably coupled with the tissue sample holder via the linking mechanism such that the thumbwheel is manually rotatable to rotate the tissue sample holder via the linking mechanism.

2. The biopsy device of claim 1, wherein a first portion of the thumbwheel protrudes from the top of the body for manual engagement by an operator.

3. The biopsy device of claim 2, wherein a second portion of the thumbwheel protrudes from the bottom of the body to engage with the linking mechanism.

4. The biopsy device of claim 1, wherein the tissue sample holder is manually rotatable to rotate the needle portion via the linking mechanism.

5. The biopsy device of claim 1, wherein the linking mechanism has a distal engagement member to rotatably engage with the thumbwheel and a proximal engagement member to rotatably engage with the tissue sample holder.

6. The biopsy device of claim 5, wherein the thumbwheel has at least one tooth around a periphery thereof to rotatably engage with the distal engagement member of the linking mechanism.

7. The biopsy device of claim 5, wherein the tissue sample holder comprises a gear configured to mesh with the proximal engagement member of the linking mechanism.

8. The biopsy device of claim 1, wherein the linking mechanism is configured to rotate the tissue sample holder in the same rotational direction as the thumbwheel.

9. The biopsy device of claim 1, the linking mechanism is configured to rotate the tissue sample holder at the same rotational rate at which the needle is rotated by the thumbwheel.

10. The biopsy device of claim 1, wherein the tissue sample holder comprises a plurality of discrete tissue sample chambers, wherein the thumbwheel is operable to successively index the sample chambers to the cutter lumen.

11. The biopsy device of claim 1, wherein the holster further comprises a cutter drive mechanism in communication with the cutter, wherein the cutter drive mechanism is operable to actuate the cutter.

12. The biopsy device of claim 11, wherein the cutter drive mechanism comprises a first drive shaft, wherein the first drive shaft has a hollow bore.

13. The biopsy device of claim 12, wherein the linking mechanism comprises a second drive shaft, wherein the second drive shaft extends longitudinally through the hollow bore of the first drive shaft.

14. The biopsy device of claim 11, wherein the cutter drive mechanism and the linking mechanism are operable independently of each other.

15. The biopsy device of claim 11, further comprising a rotary drive cable, wherein the cutter drive mechanism is driven by the rotary drive cable.

16. A biopsy device for acquiring tissue samples from a patient, the biopsy device comprising:
a needle portion having a tissue receiving aperture, wherein the needle portion defines a longitudinal axis;
a body portion having a distal end and a proximal end, wherein the needle portion extends distally from the distal end of the body portion;
a rotatable thumbwheel coupled with the needle portion, wherein the rotatable thumbwheel is fixedly secured relative to the needle portion such that the thumbwheel is operable to rotate the needle portion about the longitudinal axis;
a cutter longitudinally movable within the needle portion, wherein the cutter is configured to cut tissue protruding into the aperture, wherein the cutter defines a cutter lumen;
a rotatable tissue sample holder configured to receive tissue samples severed by the cutter and communicated through the cutter lumen;
a linking mechanism, wherein the thumbwheel is rotatably coupled with the tissue sample holder via the linking mechanism such that the thumbwheel is manually rotatable to rotate the tissue sample holder via the linking mechanism; and
a probe and a holster, wherein the probe and holster are removably coupled, wherein the needle portion, the thumbwheel, the cutter, and the tissue sample holder are provided by the probe, and wherein the linking mechanism is provided by the holster.

17. The biopsy device of claim 16, wherein the thumbwheel presents gear teeth exposed by the probe; wherein the tissue sample holder presents gear teeth exposed by the probe; wherein the linking mechanism comprises a gear train; wherein the gear train presents gear teeth exposed by the holster; wherein the gear teeth presented by the thumbwheel and the gear teeth presented by the tissue sample holder are configured to mesh with the gear teeth presented by the linking mechanism gear train when the probe is coupled with the holster.

* * * * *